United States Patent
Im et al.

(10) Patent No.: US 8,956,852 B2
(45) Date of Patent: Feb. 17, 2015

(54) HETEROTROPHIC CULTIVATION OF HYDROCARBON-PRODUCING MICROALGAE

(75) Inventors: Chung-Soon Im, Palo Alto, CA (US); Diana Vincent, San Jose, CA (US); Rika Regentin, Hayward, CA (US); Anna Coragliotti, San Francisco, CA (US)

(73) Assignee: Solazyme, Inc., South San Francisco, CA (US)

( * ) Notice: Subject to any disclaimer, the term of this patent is extended or adjusted under 35 U.S.C. 154(b) by 323 days.

(21) Appl. No.: 13/593,342

(22) Filed: Aug. 23, 2012

(65) Prior Publication Data
US 2013/0071909 A1 Mar. 21, 2013

Related U.S. Application Data

(62) Division of application No. 12/497,257, filed on Jul. 2, 2009, now Pat. No. 8,278,090.

(60) Provisional application No. 61/078,246, filed on Jul. 3, 2008.

(51) Int. Cl.
*C12N 1/12* (2006.01)
*C12P 7/64* (2006.01)

(52) U.S. Cl.
CPC .... *C12N 1/12* (2013.01); *C12P 7/64* (2013.01)
USPC ....................................... 435/257.1; 435/334

(58) Field of Classification Search
None
See application file for complete search history.

(56) References Cited

U.S. PATENT DOCUMENTS

2004/0209256 A1 10/2004 Dillon

OTHER PUBLICATIONS

US Office Action dated Mar. 21, 2012 issued in U.S. Appl. No. 12/497,257.
US Notice of Allowance dated Jul. 30, 2012 issued in U.S. Appl. No. 12/497,257.
Achitouv et al. (2004) "$C_{31}$-$C_{34}$ methylated squalenes from a Bolivian strain of *Botryococcus braunii*." *Phytochemistry* 65(23): 3159-3165.
Gusakov et al. (2007) "Design of highly efficient cellulase mixtures for enzymatic hydrolysis of cellulose" *Biotechnol Bioeng* 97(5): 1028-38.
Inoue et al. (1994) "Analysis of oil derived from liquefaction of *Botryococcus braunii*" *Biomass and Bioenergy* 6(4): 269-274.
Jeoh et al. (2007) "Cellulase digestibility of pretreated biomass is limited by cellulose accessibility" *Biotechnol Bioeng*. 98(1): 112-22.
Lane (2012) "Solazyme, Bunge form JV for commercial-scale renewable oils plant in Brazil." *Biofuels Digest* pp. 1-2.
Largeau et al. (1980) "Sites of accumulation and composition of hydrocarbons in *Botryococcus braunii*" *Phytochemistry* 19: 1043-1051.
Lawford et al. (2002) "Performance testing of *Zymomonas mobilis* metabolically engineered for cofermentation of glucose, xylose, and arabinose" *Appl Biochem Biotechnol*. 98-100: 429-48.
Metzger et al. (1985)"Alkadiene- and botryococcene-producing races of wild strains of *Botryococcus braunii*" *Phytochemistry* 24(10): 2305-2312.
Sapp (2012) "USS Ford runs on Solazyme marine diesel; first algal fuels used in operational fleet" *Biofuels Digest* pp. 1-4.
Tyystjärvi et al. (2005) "Mathematical modelling of the light response curve of photoinhibition of photosystem II." *Photosynth Res*. 84(1-3): 21-27.
Weetall et al. (1985) "Studies on the Nutritional Requirements of the Oil-Producing Alga *Botryococcus braunii*" *Applied Biochemistry and Biotechnology* 11: 377-391.
Wyman et al. (2005) "Comparative sugar recovery data from laboratory scale application of leading pretreatment technologies to corn stover" *Bioresource Technology* 96(18): 2026-32.
Zaslavskaia et al. (2001) "Trophic Conversion of an Obligate Photoautotrophic Organism Through Metabolic Engineering" *Science* 292: 2073-2075.

*Primary Examiner* — Tekchand Saidha
*Assistant Examiner* — MD. Younus Meah
(74) *Attorney, Agent, or Firm* — Jennifer L. Wahlsten; Weaver Austin Villeneuve & Sampson LLP

(57) ABSTRACT

The invention discloses novel methods of producing hydrocarbons through heterotrophic cultivation of *Botryococcus braunii*. Also provided are novel hydrocarbon compositions. A preferred species for engineering is the microalgae species *Botryococcus braunii*. Additional methods of cultivation include providing certain nutrient sources.

11 Claims, No Drawings

HETEROTROPHIC CULTIVATION OF HYDROCARBON-PRODUCING MICROALGAE

CROSS-REFERENCE TO RELATED APPLICATIONS

This application is a divisional of U.S. application Ser. No. 12/497,257, filed on Jul. 2, 2009 and issued as U.S. Pat. No. 8,278,090 on Oct. 2, 2012, which claims the benefit of U.S. Provisional Application No. 61/078,246, filed Jul. 3, 2008, both of which are hereby incorporated by reference in their entireties.

GOVERNMENT INTERESTS

This invention was made with United States Government support under Cooperative Agreement Award Number 70NANB7H7002 awarded by the National Institute of Standards and Technology (NIST).

The United States Government has certain rights in the invention.

FIELD OF THE DISCLOSED INVENTION

This disclosure relates to hydrocarbon compositions and the means for their production. Compositions containing one or more novel hydrocarbons produced by one or more microorganisms, optionally with additional modification in vitro, are disclosed herein. Also disclosed are methods for the preparation of the hydrocarbon compositions, for example by heterotrophic growth of microorganisms, such as the microalgae *Botryococcus braunii*. Also disclosed are methods of genetically engineering hydrocarbon-producing microalgae.

BACKGROUND

Fossil fuel is a general term for buried combustible geologic deposits of organic materials, formed from decayed plants and animals that have been converted to crude oil, coal, natural gas, or heavy oils by exposure to heat and pressure in the earth's crust over hundreds of millions of years.

In common dialogue, fossil fuel, also known as mineral fuel, is used synonymously with other hydrocarbon-containing natural resources such as coal, oil and natural gas. The utilization of fossil fuels has enabled large-scale industrial development and largely supplanted water driven mills, as well as the combustion of wood or peat for heat. Fossil fuels are a finite, non-renewable resource.

When generating electricity, energy from the combustion of fossil fuels is often used to power a turbine. Older generators often used steam generated by the burning of the fuel to turn the turbine, but in newer power plants the gases produced by burning of the fuel turn a gas turbine directly. With global modernization in the 20th and 21st centuries, the thirst for energy from fossil fuels, especially gasoline derived from oil, is one of the causes of major regional and global conflicts.

The burning of fossil fuels by humans is the largest source of emissions of carbon dioxide, which is one of the greenhouse gases that allows radiative forcing and contributes to global warming. In the United States, more than 90% of greenhouse gas emissions come from the combustion of fossil fuels. In addition other air pollutants, such as nitrogen oxides, sulfur dioxide, VOCs, and heavy metals are produced.

Human activity raises levels of greenhouse gases primarily by releasing carbon dioxide from fossil fuel combustion, but other gases, e.g. methane, are not negligible. The concentrations of several greenhouse gases have increased over time due to human activities, such as burning of fossil fuels and deforestation leading to higher carbon dioxide concentrations. According to the global warming hypothesis, greenhouse gases from industry and agriculture have played a major role in the recently observed global warming.

BRIEF SUMMARY OF THE DISCLOSED INVENTION

In certain embodiments, the invention provides a method for culturing *Botryococcus braunii* microalgae heterotrophically. The method entails:
(a) providing culture media that includes a fixed carbon source in a fermentor;
(b) inoculating the fermentor with a strain of *Botryococcus braunii* microalgae capable of metabolizing the fixed carbon source;
(c) culturing the microalgae in heterotrophic conditions for a period of time sufficient to produce growth and/or propagation of the microalgae, wherein the fermentor does not allow light to strike the microalgae.

In particular embodiments, the conditions within the fermentor are such that the microalgae generally do not carry out photosynthesis during culturing.

The fixed carbon source used in the method can be a carbohydrate, such as glucose, mannose, galactose, or fructose, but is not limited to such. An exemplary non-carbohydrate carbon source useful in the invention is glycerol. Such suitable carbon sources can be used individually or in combination.

In certain embodiments, the culturing is carried out for a period of time sufficient to produce growth and/or propagation of the microalgae whereby the dry cell weight of microalgae at the end of culturing (as compared to the approximate dry cell weight of microalgae in the inoculum) is increased by at least about 2-, about 3-, about 4-, about 5-, about 6-, about 7-, about 8-, about 9-, or about 10-fold or more, or by an amount within any range having any of these values as endpoints.

In particular embodiments, the culture medium can be provided with a complex nitrogen source before or during culturing. Exemplary complex nitrogen sources that are useful in the invention include urea, hydrolysate casein, and a combination thereof.

The inoculum added to the fermentor can be produced, in particular embodiments, by culture of *B. braunii* in the dark for at least one passage prior to addition to the fermentor. The inoculum can be produced by prior culture in the dark for a plurality of passages, e.g., 2 passages, 3 passages, 4 passages, or 5 or more passages. In certain embodiments, after culturing the microalgae in the fermentor for a period of time in the dark, all or a portion of the microalgae can be transferred to a further fermentor, where the microalgae can be further cultured for a period of time, wherein the further fermentor does not allow light to strike the microalgae.

Another aspect of the invention is a method of producing hydrocarbons from *Botryococcus braunii* microalgae that have be cultured heterotrophically according to the above method of the invention. Hydrocarbons are produced by culturing, according to this method, for a period of time to generate microalgal biomass, and extracting hydrocarbons from the microalgal biomass. Any suitable extraction method can be employed, such as hexane extraction, pressing biomass, and in vivo extraction. In particular embodiments, the method can additionally include separating different species of extracted hydrocarbons, e.g., in a fractional distillation column.

The invention also provides a culture of *Botryococcus braunii* microalgae produced according to the above culture method of the invention, as well as a hydrocarbon extract produced from a microalgal biomass that is produced according to this culture method.

In certain embodiments of the culture method of the invention, the dry cell weight of the microalgae is greater than the dry cell weight of the same strain of microalgae cultured in the presence of light, with all other culture conditions being the same. The dry cell weight of microalgae grown using a fixed carbon source in the dark can exceed the dry cell weight of microalgae grown using the same fixed carbon source in the light by at least: about 2-, about 3-, about 4-, about 5-fold or more, or by an amount within any range having any of these values as endpoints.

BRIEF DESCRIPTION OF THE DRAWINGS

Not Applicable

DETAILED DESCRIPTION OF THE DISCLOSED INVENTION

Definitions

"Active in microalgae" means a nucleic acid that is functional in microalgae. For example, a promoter that has been used to drive an antibiotic resistance gene to impart antibiotic resistance to a transgenic microalgae is active in microalgae. Examples of promoters active in microalgae are promoters endogenous to certain algae species and promoters found in plant viruses.

"Aqueous fraction" refers to the portion, or fraction, of a material that is more soluble in an aqueous phase in comparison to a hydrophobic phase. An aqueous phase is readily water soluble.

"Axenic" means a culture of an organism that is free from contamination by other living organisms.

"Fermentor" or "bioreactor" means an enclosure or partial enclosure in which cells are cultured, optionally in suspension. A fermentor or bioreactor of the disclosure includes non-limiting embodiments such as an enclosure or partial enclosure which permits cultured cells to be exposed to light or which allows the cells to be cultured without exposure to light. The term "fermenter" is either synonymous with "fermentor" or refers to a microbial organism that causes fermentation. The interpretation of "fermenter" is as consistent with the context in which the term is used.

The term "biomass" refers to material produced by growth and/or propagation of cells. Biomass may contain cells and/or intracellular contents as well as extracellular material. Extracellular material includes, but is not limited to, compounds secreted by a cell.

"Carbohydrate" refers to one or more molecules usually consisting of carbon, hydrogen, and oxygen. Representative carbohydrates are glucose, xylose, and glycerol. The term "carbohydrate" as used herein can refer to a mixture of different carbohydrate species such as depolymerized cellulose, which comprises glucose, xylose, and partially depolymerized cellulose fragments such as oligosaccharides and disaccharides, as well as lignin.

"Carbohydrate transporter" refers to a polypeptide located in or adjacent to a lipid bilayer and facilitates the transport of carbohydrates across the lipid bilayer.

As used herein, a "catalyst" refers to an agent, such as a molecule or macromolecular complex, capable of facilitating or promoting a chemical reaction of a reactant to a product without becoming a part of the product. A catalyst thus increases the rate of a reaction, after which, the catalyst may act on another reactant to form the product. A catalyst generally lowers the overall activation energy required for the reaction such that it proceeds more quickly or at a lower temperature. Thus a reaction equilibrium may be more quickly attained. Examples of catalysts include enzymes, which are biological catalysts, and heat, which is a non-biological catalyst.

"Cell material" refers to material containing cells and/or intra- and extracellular contents, such as from the disruption of cells. Unprocessed material contains both hydrophobic and aqueous fractions from cells. Cell material includes biomass as well as disrupted or homogenized biomass.

"Conditions favorable to cell division" means conditions in which cells divide at least once every 72 hours.

The term "heterotrophic conditions" refers to the presence of at least one fixed carbon source and the absence of light during culturing.

The term "co-culture", and variants thereof such as "co-cultivate", refer to the presence of two or more types of cells in the same fermentor or bioreactor. The two or more types of cells may both be microorganisms, such as microalgae, or may be a microalgal cell cultured with a different cell type. The culture conditions may be those that foster growth and/or propagation of the two or more cell types or those that facilitate growth and/or proliferation of one, or a subset, of the two or more cells while maintaining cellular growth for the remainder.

The phrase "covalently modifies", and variants thereof, refer to the formation of, removal or, or alteration in, one or more covalent bonds in a molecule. In the practice of the disclosed invention, the formation of, removal of, or alteration in, a covalent bond of a hydrocarbon molecule is expressly contemplated and disclosed.

The term "cultivated", and variants thereof, refer to the intentional fostering of growth (increases in cell size, cellular contents, and/or cellular activity) and/or propagation (increases in cell numbers via mitosis) of one or more cells by use of intended culture conditions. The combination of both growth and propagation may be termed proliferation. The one or more cells may be those of a microorganism, such as microalgae. Examples of intended conditions include the use of a defined medium (with known characteristics such as pH, ionic strength, and carbon source), specified temperature, oxygen tension, carbon dioxide levels, and growth in a fermentor or bioreactor. The term does not refer to the growth of microorganisms in nature or otherwise without direct human intervention, such as natural growth of an organism that ultimately becomes fossilized to produce geological crude oil.

"Distillation column" means a device for separating hydrocarbons based on evaporation temperature, such as within a facility for refining crude oil into gasoline.

"Exogenous gene" refers to a nucleic acid transformed into a cell. A transformed cell may be referred to as a recombinant cell, into which additional exogenous gene(s) may be introduced. The exogenous gene may be from a different species (and so heterologous), or from the same species (and so homologous) relative to the cell being transformed. In the case of a homologous gene, it occupies a different location in the genome of the cell relative to the endogenous copy of the gene. The exogenous gene may be present in more than one copy in the cell. The exogenous gene may be maintained in a cell as an insertion into the genome or as an episomal molecule.

"Exogenously provided" describes a molecule provided to the culture media of a cell culture.

"Fixed carbon source" means molecule(s) containing carbon, preferably organic, that are present at ambient temperature and pressure in solid or liquid form.

"Homogenate" means biomass that has been disrupted.

"Hydrophobic fraction" refers to the portion, or fraction, of a material that is more soluble in a hydrophobic phase in comparison to an aqueous phase. A hydrophobic fraction is substantially insoluble in water and usually non-polar.

As used herein, "hydrocarbon" refers to: (a) a molecule containing only hydrogen and carbon atoms wherein the carbon atoms are covalently linked to form a linear, branched, cyclic, or partially cyclic backbone to which the hydrogen atoms are attached; or (b) a molecule that only primarily contains hydrogen and carbon atoms and that can be converted to contain only hydrogen and carbon atoms by one or two chemical reactions. Nonlimiting examples of the latter include hydrocarbons containing an oxygen atom between one carbon and one hydrogen atom to form an alcohol molecule, as well as aldehydes containing a single oxygen atom. Methods for the reduction of alcohols to hydrocarbons containing only carbon and hydrogen atoms are well known. Another example of a hydrocarbon is an ester, in which an organic group replaces a hydrogen atom (or more than one) in an oxygen acid. The molecular structure of hydrocarbon compounds varies from the simplest, in the form of methane ($CH_4$), which is a constituent of natural gas, to the very heavy and very complex, such as some molecules such as asphaltenes found in crude oil, petroleum, and bitumens. Hydrocarbons may be in gaseous, liquid, or solid form, or any combination of these forms, and may have one or more double or triple bonds between adjacent carbon atoms in the backbone. Accordingly, the term includes linear, branched, cyclic, or partially cyclic alkanes, alkenes, lipids, and paraffin. Examples include propane, butane, pentane, hexane, octane, squalene and carotenoids.

"Hydrocarbon modification enzyme" refers to an enzyme that alters the covalent structure of a hydrocarbon. An example of a hydrocarbon modification enzyme is an aldehyde decarbonylase.

The term "hydrogen:carbon ratio" refers to the ratio of hydrogen atoms to carbon atoms in a molecule on an atom-to-atom basis. The ratio may be used to refer to the number of carbon and hydrogen atoms in a hydrocarbon molecule. For example, the hydrocarbon with the highest ratio is methane $CH_4$ (4:1).

The term "in situ" means "in place" or "in its original position". For example, a culture containing a first microalgae secreting a catalyst and a second microorganism secreting a substrate, wherein the first and second cell types produce the components necessary for a particular chemical reaction to occur in situ in the co-culture without requiring further separation or processing of the materials.

"Microalgae" means a microbial organism that is capable of performing photosynthesis. Microalgae include obligate photoautotrophs, which cannot metabolize a fixed carbon source as energy, as well as heterotrophs, which can live solely off of light, solely off of a fixed carbon source, or a combination of the two. Microalgae can refer to unicellular organisms that separate from sister cells shortly after cell division, such as *Chlamydomonas*, and can also refer to microbes such as, for example, Volvox, which is a simple multicellular photosynthetic microbe of two distinct cell types. "Microalgae" can also refer to cells such as *Botryococcus*, which associate with each other through extracellular matrices made of hydrocarbons and biopolymers such as polysaccharides. "Microalgae" also includes other microbial photosynthetic organisms that exhibit cell-cell adhesion, such as *Agmenellum, Anabaena*, and *Pyrobotrys*.

"Mutagenize" means to alter the sequence of the genome of an organism. Mutagenesis can be through random means, such as chemical mutagenesis or vector insertion. A vector used for insertion can contain only a screenable or selectable marker, or can also contain a nucleic acid sequence designed to express a gene, such as a cDNA or an antisense or RNAi construct. Mutagenesis can also be through directed means, such as through homologous recombination.

"Wastewater" is watery waste which typically contains washing water, laundry waste, faeces, urine and other liquid or semi-liquid wastes. It includes some forms of municipal waste as well as secondarily treated sewage.

"Naturally produced" describes a compound that can be produced by a wild-type organism.

"Photobioreactor" or "photofermentor" refers to a container, at least part of which is at least partially transparent or partially open, thereby allowing light to pass through, in which one or more microalgae cells are cultured. Photobioreactors or photofermentors may be closed, as in the instance of a polyethylene bag or Erlenmeyer flask, or may be open to the environment, as in the instance of an outdoor pond.

"Port", in the context of a fermentor, bioreactor, photofermentor, or photobioreactor, refers to an opening in the photobioreactor that allows influx or efflux of materials such as gases, liquids, and cells. Ports are usually connected to tubing leading from the fermentor, bioreactor, photofermentor, or photobioreactor.

The term "transport protein" refers to a polypeptide located in or adjacent to a lipid bilayer and facilitates the transport of molecules or ions across the lipid bilayer.

"Vessel" refers to a container for use in performing biochemical reactions, chemical separations, microbial cultivation, and other functions.

For sequence comparison to determine percent nucleotide or amino acid identity, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

Another example of algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (at the web address www.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. For identifying whether a nucleic acid or polypeptide is within the scope of the invention, the default parameters of the BLAST programs are suitable. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix. The TBLATN program (using protein sequence for nucleotide sequence) uses as defaults a word length (W) of 3, an expectation (E) of 10, and a BLOSUM 62 scoring matrix. (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

I General

The invention is premised in part on the insight that certain microorganisms can be used to produce hydrocarbon compositions economically and in large quantities for use in the transportation fuel and petrochemical industry among other applications. For example, the microalgae *Botryococcus braunii* produces a high yield of up to 86% crude weight of long chain hydrocarbons, a composition that is similar to high grade crude oil. However, this microorganism has evolved in nature for survival in the wild rather than for rapid growth in a laboratory and was previously believed to grow too slowly in its wild-type state to produce a commercially viable source of hydrocarbons. Surprisingly, it has been found that this species, which was known as an obligate autotroph, exhibits good growth when cultured in the dark with a fixed carbon source.

Other microorganisms have naturally evolved for rapid growth in harsh conditions in the wild (e.g., sewage processing pools) but do not produce hydrocarbons in useful quantities.

The present application describes novel methods for culturing, as well as methods for genetic modification of *Botryococcus braunii* and similar organisms, to improve the rate and economics of growth in a cell culture environment. The invention also provides methods of modifying other microorganisms that already have desired growth characteristics to acquire characteristics for producing large quantities of useful hydrocarbons.

The resulting organisms having both high yields of useful hydrocarbons and desired growth characteristics provide an alternative source of hydrocarbons to the conventional petrochemical and oil industry. These hydrocarbons can be harvested from cell cultures and subjected to catalysis to produce crude oil, gasoline, terpenoids, pharmaceutical precursors, rubber precursors and specialty chemical products. Some microalgae described herein can also be used for production of hydrocarbons such as lutein.

Further, the invention provides genetically engineering strains of microalgae with two or more exogenous genes. The first gene encodes a transporter of a fixed carbon source and the second gene encodes a carbohydrate modification enzyme. The resulting fermentable organisms produce greater amounts of hydrocarbons per unit time as well as hydrocarbon compositions that contain greater energy content per unit weight than what has been obtainable by previously known methods of geological or biological hydrocarbon production. By providing the ability to metabolize a fixed carbon source rather than only sunlight and carbon dioxide and the ability to steer metabolic carbon flux into high-energy content molecules at levels far greater than can be achieved in non-engineered organisms, the invention provides energy production methods far superior that those so far known. In other words, providing saturating amounts of usable fixed carbon and inserting exogenous genes encoding enzymes that steer the fixed carbon into specific energy-containing hydrocarbons allows for production of liquid hydrocarbons for transportation and other fuels at levels never before possible using microorganisms. Optionally, the insertion of the two exogenous genes described above can be combined with the disruption of polysaccharide biosynthesis through directed and/or random mutagenesis, which steers ever greater carbon flux into hydrocarbon production.

Individually and in combination, trophic conversion, engineering to alter hydrocarbon production, and treatment with exogenous enzymes alter the hydrocarbon composition produced by a microorganism. The alteration can be a change in the amount of hydrocarbons produced, the amount of one or more hydrocarbon species produced relative to other hydrocarbons, and/or the types of hydrocarbon species produced in the microorganism.

II Hydrocarbons

Hydrocarbons form a heterogeneous group of molecules of different sizes, shapes and/or lengths, and molecular weight. They are constructed primarily or exclusively from hydrogen and carbon atoms wherein the carbon atoms are covalently linked to form a linear, branched, cyclic, or partially cyclic backbone. The hydrogen atoms are attached to the carbon atoms in the backbone. By structure, hydrocarbons are characterized by two main classes: aliphatic and aromatic. Aliphatic hydrocarbons include alkanes, alkenes, and alkynes as well as their cyclic counterparts, which may be referred to as cyclic aliphatic hydrocarbons. Generally, aliphatic compounds are open-chain in structure, such as linear, or are cyclic compounds that resemble the open-chain structures.

Aromatic compounds are benzene and compounds that chemically resemble benzene in behavior. Although aliphatic hydrocarbons generally undergo addition (at locations of multiple bonds) and free-radical substitution (at other locations along the aliphatic chain), aromatic hydrocarbons tend to undergo heterolytic substitution. Aromatic compounds are also characterized by their resonance structure.

Hydrocarbons can be used as an energy source based on the heat released on combustion. Examples include the combustion of methane, ethane, propane and butane as gases, as well as the combustion of larger hydrocarbons in the gaseous or liquid forms. Hydrocarbons have also been utilized as the precursors, or subunits, for the production of polymers such as plastics.

Aliphatic alkanes are represented by the general formula $C_nH_{2n+2}$, which indicates the number of carbon and hydrogen atoms in an alkane molecule. This formula can also be used as an example of the highest possible hydrogen to carbon (hydrogen:carbon) ratio in a hydrocarbon of a given carbon backbone structure. The higher the ratio, the more energy released upon combustion. Hydrocarbons with a hydrogen to carbon ratio above about 2 are preferred for combustion. A cyclic aliphatic hydrocarbon is represented by the general formula $C_nH_{2n}$.

In an alkane, the carbon atoms in the carbon-carbon backbone are linked via carbon-carbon single bonds. Alkenes contain less hydrogen, on a carbon for carbon basis, than the alkanes. Thus, an alkene can be converted to an alkane by addition of hydrogen. Conversely, an alkane can be converted to an alkene by the loss of hydrogen. An alkene contains less than the maximum amount of hydrogen on a carbon-carbon backbone, so an alkene is referred to as an unsaturated hydrocarbon. The unsaturated condition is present in the carbon-carbon backbone of an alkene in the form of one or more carbon-carbon double bonds. The simplest alkene is ethylene.

Alkynes are another type of unsaturated hydrocarbon. In an alkyne, the carbon-carbon backbone contains one or more carbon-carbon triple bonds. Like a double bond, the triple bond is highly reactive. The simplest alkyne is acetylene.

Terpenes are one type of hydrocarbon. Terpenes are compounds found in the essential oils of various plants and among the hydrocarbons of various microorganism. Terpenes are derived from isoprene, which may be considered the unit upon which a terpene is based. Isoprene has the molecular formula $C_5H_8$ and terpenes are represented by a formula for multiples of that. Thus $(C_5H_8)_n$ where n is the number of linked isoprene units is a formula which generally represents terpene structure. This relationship between terpenes and isoprene is also referred to as the isoprene rule or the $C_5$ rule. In some terpenes, the individual isoprene units may be linked "head to tail" to form linear chains. In other terpenes, the isoprene units are arranged to form rings.

Terpenes can be modified chemically to form terpenoids for example by oxidation or rearrangement of the carbon backbone of terpene. Examples of terpenes include hemiterpenes, with one isoprene unit where oxygen-containing derivatives like prenol and isovaleric acid are hemiterpenoids; monoterpenes, with two isoprene units and represented by the formula $C_{10}H_{16}$; sesquiterpenes, with three isoprene units and represented by the formula $C_{15}H_{24}$; diterpenes, with four isoprene units and represented by the formula $C_{20}H_{32}$; sesterterpenes, with 25 carbons and five isoprene units; triterpenes, with six isoprene units and represented by the formula $C_{30}H_{48}$; tetraterpenes, with eight isoprene units and represented by the formula $C_{40}H_{56}$; and polyterpenes, with long chains of many isoprene units.

Examples of diterpenes include cembrene and taxadiene. Diterpenes are also the basis for biological compounds such as retinol, retinal, and phytol. A non-limiting example of a triterpene is the linear triterpene squalene. Examples of tetraterpenes include the acyclic lycopene, the monocyclic gamma-carotene, and the bicyclic alpha- and beta-carotenes. A representative example of a polyterpene is rubber, consisting of polyisoprene in which the double bonds are cis.

Lipids are another type of hydrocarbon containing molecule. Examples of lipids include fatty acids (saturated and unsaturated); glycerides or glycerolipids (such as monoglycerides, diglycerides, triglycerides or neutral fats, and phosphoglycerides or glycerophospholipids); nonglycerides (sphingolipids, sterol lipids including cholesterol and steroid hormones, prenol lipids including terpenoids, waxes, and polyketides); and complex lipid derivatives (sugar-linked lipids, or glycolipids, and protein-linked lipids). In some embodiments, the lipid is a phospholipid, such as farnesyl diphosphate.

Long chain hydrocarbons are particularly useful for the petrochemical industry. In some embodiments, a long chain hydrocarbon contains at least about 8, at least about 10, at least about 12, at least about 14, at least about 16, at least about 18, at least about 20, at least about 22, at least about 24, at least about 26, at least about 28, at least about 30, at least about 32, or at least about 34 carbon atoms or more. Other embodiments include hydrocarbons, such as the above long chain hydrocarbons, that are alkanes (with no carbon-carbon double or triple bonds); that are linear (not cyclic); and/or that have little or no branching in their structures. Hydrocarbons with a hydrogen:carbon ratio above about 2, up to 4 in the case of methane, are included as embodiments herein.

Different hydrocarbon chain lengths all have progressively higher boiling points, so they can all be separated by distillation. For example, crude oil is separated into various fractions by heating and separating different chain lengths when they vaporize at different temperatures. Each different chain length has a different property that makes it useful in a different way. Petroleum gas used for heating, cooking, and making plastics contains small alkanes (1 to 4 carbon atoms), e.g., methane, ethane, propane, butane having a boiling range less than 40 degrees. Naphtha or ligroin are intermediates further processed to make gasoline. They contain 5 to 9 carbon atom alkanes and have a boiling range of 60 to 100 degrees Celsius. Gasoline has a mix of alkanes and cycloalkanes of 5 to 12 carbon atoms and a boiling range of 40 to 205 degrees Celsius. Kerosene, which is the fuel for jet engines and tractors and a starting material for making other products is a mix of alkanes of 10 to 18 carbons and aromatics and has a boiling range of 175 to 325 degrees Celsius. Gas oil or diesel distillate, which is used for diesel fuel and heating oil; starting material for making other products contains alkanes containing of 12 or more carbon atoms and has a boiling range of 250 to 350 degrees Celsius. Lubricating oil, which is used for motor oil, grease, and other lubricants contains long chains of 20 to 50 carbon atoms and includes alkanes, cycloalkanes, aromatics, and has a boiling range of 300 to 370 degrees Celsius. Heavy gas or fuel oil, which is used for industrial fuel and as a starting material for making other products contains long chain of 20 to 70 carbon atoms including alkanes, cycloalkanes, aromatics and has a boiling range of 370 to 600 degrees Celsius. Residuals include coke, asphalt, tar, waxes; starting material for making other products, which are multiple-ringed compounds with 70 or more carbon atoms and a boiling range greater than 600 degrees Celsius. It is an object of the invention to provide genetically engineered microorganisms, particularly microalgae, that produce one or more species of hydrocarbons disclosed in this and the previous paragraph, as well as precursors to these molecules that can be put through refining and/or catalysis and/or cracking to produce the molecules disclosed in this and the previous paragraph.

III Suitable Microorganisms

Desired microorganisms for use in the invention produce high yields of hydrocarbons, and/or grow rapidly on a fixed carbon source. Any species of organism that produces hydrocarbons can be used, although microorganisms that naturally produce high levels of hydrocarbons are preferred. Production of hydrocarbons by microorganisms is reviewed by Metzger et al. Appl Microbiol Biotechnol (2005) 66: 486-496. Nonlimiting examples of photosynthetic microorganisms, listed as both genus and species, that can be used can be found in Table I.

TABLE I

Achnanthes orientalis
Agmenellum
Amphiprora hyaline
Amphora coffeiformis
Amphora coffeiformis linea
Amphora coffeiformis punctata
Amphora coffeiformis taylori
Amphora coffeiformis tenuis
Amphora delicatissima
Amphora delicatissima capitata
Amphora sp.
Anabaena
Ankistrodesmus
Ankistrodesmus falcatus
Boekelovia hooglandii
Borodinella sp.
Botryococcus braunii
Botryococcus sudeticus
Carteria
Chaetoceros gracilis
Chaetoceros muelleri
Chaetoceros muelleri subsalsum
Chaetoceros sp.
Chlorella ellipsoidea
Chlorella salina
Chlorella sp.
Chlorococcum infusionum
Chlorococcum sp.
Chlorogonium
Chroomonas sp.
Chrysosphaera sp.
Cricosphaera sp.
Cryptomonas sp.
Cyclotella cryptica
Cyclotella meneghiniana
Cyclotella sp.
Dunaliella sp.
Dunaliella bardawil
Dunaliella bioculata
Dunaliella granulata
Dunaliella maritima
Dunaliella minuta
Dunaliella parva
Dunaliella peircei
Dunaliella primolecta
Dunaliella salina
Dunaliella terricola
Dunaliella tertiolecta
Dunaliella viridis
Dunaliella tertiolecta
Eremosphaera viridis
Eremosphaera sp.
Ellipsoidon sp.
Euglena
Franceia sp.
Fragilaria crotonensis
Fragilaria sp.
Gleocapsa sp.
Gloeothamnion sp.
Hymenomonas sp.
Isochrysis aff. galbana
Isochrysis galbana
Lepocinclis
Monoraphidium minutum
Monoraphidium sp.

TABLE I-continued

Nannochloris sp.
Nannochloropsis salina
Nannochloropsis sp.
Navicula acceptata
Navicula biskanterae
Navicula pseudotenelloides
Navicula saprophila
Navicula sp.
Nephrochloris sp.
Nephroselmis sp.
Nitschia communis
Nitzschia alexandrina
Nitzschia communis
Nitzschia dissipata
Nitzschia frustulum
Nitzschia hantzschiana
Nitzschia inconspicua
Nitzschia intermedia
Nitzschia microcephala
Nitzschia pusilla
Nitzschia pusilla elliptica
Nitzschia pusilla monoensis
Nitzschia quadrangula
Nitzschia sp.
Ochromonas sp.
Oocystis parva
Oocystis pusilla
Oocystis sp.
Oscillatoria limnetica
Oscillatoria sp.
Oscillatoria subbrevis
Pascheria acidophila
Pavlova sp.
Phagus
Phormidium
Platymonas sp.
Pleurochrysis carterae
Pleurochrysis dentate
Pleurochrysis sp.
Pyramimonas sp.
Pyrobotrys
Sarcinoid chrysophyte
Spirogyra
Stichococcus sp.
Synechococcus sp.
Tetraedron,
Tetraselmis sp.
Tetraselmis suecica
Thalassiosira weissflogii

*Botryococcus*, particularly *Botryococcus braunii*, is a preferred microorganism because of its high yield and composition of hydrocarbons, particularly long chain hydrocarbons. *Pyrobotrys, Phormidium, Agmenellum, Carteria, Lepocinclis, Pyrobotrys, Nitzschia, Lepocinclis, Anabaena, Euglena, Spirogyra, Chlorococcum, Tetraedron, Oscillatoria, Phagus* and *Chlorogonium* are also useful because of their capacity to grow rapidly in the harsh conditions of wastewater and sewage treatment pools and their ability to recycle waste products.

Non-photosynthetic microorganisms can also be used to produce hydrocarbons, such as *E. coli, Bacillus, Saccromyces*, and other microbes that are preferably amenable to genetic engineering. For example, *E. coli* has been used to manufacture hydrocarbons such as carotenoids (see for example Appl Microbiol Biotechnol. 2006 Apr. 14, Characterization of bacterial beta-carotene 3,3'-hydroxylases, CrtZ, and P450 in astaxanthin biosynthetic pathway and adonirubin production by gene combination in *Escherichia coli*, Choi S K et al.). Such microorganisms include obligate heterotrophs which naturally produce hydrocarbons. Alternatively, heterotrophs can be recombinantly modified to enhance production of a hydrocarbon. For example, heterotrophs can be transformed with a nucleic acid sequence that encodes a beta carotene hydroxylase.

IV Trophic Conversion

Trophic conversion refers to the process of recombinantly inserting a nucleic acid sequence into a photoautotrophic cell such that it gains the capability of relying upon a fixed carbon source (see Zaslayskaia et al. Science (2001) 292:2073-2075). Some microorganisms including *Botryococcus braunii* are photoautotrophic organisms, meaning that these organisms in their wild-type state rely upon light as an energy source and carbon dioxide as a carbon source for cellular activities and functions. An obligate photoautotroph is unable to utilize a fixed carbon source in its environment as an energy source. This is in contrast to heterotrophic organisms which can utilize a fixed carbon source (such as glucose) as an energy source. Mixotrophic organisms are capable of deriving metabolic energy both from photosynthesis and from external energy sources. Some microalgae such as *Chlorella* can grow heterotrophically (in the dark on a fixed carbon source), photoautotrophically (using only light as an energy source), or mixotrophically (in the presence of both light and a fixed carbon source). In the presence of light, *Botryococcus braunii* growth can be inhibited by the inclusion of carbohydrates in the culture medium. However, the inventors have discovered that this species can utilize fixed carbon sources, including carbohydrates, and exhibits good growth characteristics when cultured in the absence of light.

In many instances, the inability of photoautotrophs to use a fixed carbon source arises from lack of a transporter to take up the source into the cell. Many cells lacking such a transporter can nevertheless metabolize a fixed carbon source once it is taken up into the cell.

Photoautotrophs can be converted to heterophophic or mixotrophic organisms by genetic transformation. This added function confers the ability for the cell to grow and propagate in the absence of light and photosynthesis (such as in the dark) but in the presence of the fixed carbon source. The nucleic acid sequence can be a gene encoding a membrane-associated transporter that transports a fixed carbon source, such as glucose, into the cell. In some instances two genes are required to trophically convert a photoautotroph: a first gene encoding a transporter that transports a fixed carbon source into the cell, and a second gene encoding an enzyme with hexokinase activity that phosphorylates a hexose molecule such as glucose. Some organisms require an exogenous hexokinase gene to convert a fixed carbon source into a phosphorylated form that can be utilized by the endogenous metabolic pathways of the cell. Many obligate photoautotrophs contain endogenous genes encoding enzymes with hexokinase activity. Whether a hexokinase gene is required for trophic conversion can be determined by radiolabeling a fixed carbon source such as glucose and exposing cells expressing a transporter to the radiolabeled glucose. Cells that transport the labeled glucose but are not capable of growth in the absence of light can be trophically converted by being transformed by a second gene encoding a hexokinase, followed by selection in the dark on media containing glucose. The gene encoding the transporter or other gene is in operable linkage to a promoter active in microalgae and optionally other regulatory sequences, such as introns and enhancers, that allow or facilitate expression. Trophic conversion provides advantages such as increased, or faster, growth rates, shorter growth times, and very high cell densities in culture. The need for light energy is reduced or eliminated because the cells may grow and produce cellular products, including hydrocarbons, in the presence of fixed carbon material as the energy source.

Preferred cells for trophic conversion include *Pyrobotrys, Phormidium, Agmenellum, Carteria, Lepocinclis, Pyrobotrys, Nitzschia, Lepocinclis, Anabaena, Euglena, Spirogyra, Chlorococcum, Tetraedron, Oscillatoria, Phagus, Chlorogonium, Dunaliella* or *Botryococcus* cells. Optionally, such cells are transformed with one or more transporters having substrate specificities that allow transport of multiple carbon sources, such as those found in municipal wastewater and/or secondarily treated sewage. Examples of such multisubstrate transporters are described herein in the sequence listing. Other such cells can be produced by chemical or nonchemical mutagenesis of natural cells or cells transformed with a transporter. Transformed cells are selected on a carbon source in the absence of light. The selection can be, for example, on about 0.1% or about 1% glucose, or another fixed carbon source, in the dark. Alternatively, the microalgae can be transformed with a vector containing both an antibiotic resistance gene, such as a gene encoding resistance to the antibiotic zeocin, and a carbohydrate transporter with selection for antibiotic resistance. New strains exhibiting antibiotic resistance can be then tested for the ability to grow in the dark in the presence of a fixed carbon source that is transported by the carbohydrate transporter. Carbon sources suitable for use in the invention can be found below in Table II. A preferred carbon source is depolymerized cellulose in the form of a mixture of xylose and glucose, optionally including arabinose, as described for example in Wyman et al., Comparative sugar recovery data from laboratory scale application of leading pretreatment technologies to corn stover, Bioresour Technol. 2005 December; 96(18):2026-32; Gusakov et al., Design of highly efficient cellulase mixtures for enzymatic hydrolysis of cellulose, Biotechnol Bioeng 2007 Jan. 12; Jeoh et al., Cellulase digestibility of pretreated biomass is limited by cellulose accessibility, Biotechnol Bioeng. 2007 Mar. 2; Lawford et al., Performance testing of *Zymomonas mobilis* metabolically engineered for cofermentation of glucose, xylose, and arabinose, Appl Biochem Biotechnol. 2002 Spring; 98-100:429-48.

TABLE II 2,3-Butanediol
2-Aminoethanol
2'-Deoxy Adenosine
3-Methyl Glucose
Acetic Acid
Adenosine
Adenosine-5'-Monophosphate
Adonitol
Amygdalin
Arbutin
Bromosuccinic Acid
Cis-Aconitic Acid
Citric Acid
D,L-Carnitine
D,L-Lactic Acid
D,L-α-Glycerol Phosphate
D-Alanine
D-Arabitol
D-Cellobiose
Dextrin
D-Fructose
D-Fructose-6-Phosphate
D-Galactonic Acid Lactone
D-Galactose
D-Galacturonic Acid
D-Gluconic Acid
D-Glucosaminic Acid
D-Glucose-6-Phosphate
D-Glucuronic Acid
D-Lactic Acid Methyl Ester
D-L-α-Glycerol Phosphate
D-Malic Acid
D-Mannitol
D-Mannose
D-Melezitose

TABLE II-continued

D-Melibiose
D-Psicose
D-Raffinose
D-Ribose
D-Saccharic Acid
D-Serine
D-Sorbitol
D-Tagatose
D-Trehalose
D-Xylose
Formic Acid
Gentiobiose
Glucuronamide
Glycerol
Glycogen
Glycyl-LAspartic Acid
Glycyl-LGlutamic Acid
Hydroxy-LProline
i-Erythritol
Inosine
Inulin
Itaconic Acid
Lactamide
Lactulose
L-Alaninamide
L-Alanine
L-Alanylglycine
L-Alanyl-Glycine
L-Arabinose
L-Asparagine
L-Aspartic Acid
L-Fucose
L-Glutamic Acid
L-Histidine
L-Lactic Acid
L-Leucine
L-Malic Acid
L-Ornithine
L-Phenylalanine
L-Proline
L-Pyroglutamic Acid
L-Rhamnose
L-Serine
L-Threonine
Malonic Acid
Maltose
Maltotriose
Mannan
m-Inositol
N-Acetyl-DGalactosamine
N-Acetyl-DGlucosamine
N-Acetyl-LGlutamic Acid
N-Acetyl-β-DMannosamine
Palatinose
Phenyethylamine
p-Hydroxy-Phenylacetic Acid
Propionic Acid
Putrescine
Pyruvic Acid
Pyruvic Acid Methyl Ester
Quinic Acid
Salicin
Sebacic Acid
Sedoheptulosan
Stachyose
Succinamic Acid
Succinic Acid
Succinic Acid Mono-Methyl-Ester
Sucrose
Thymidine
Thymidine-5'-Monophosphate
Turanose
Tween 40
Tween 80
Uridine
Uridine-5'-Monophosphate
Urocanic Acid
Water
Xylitol
α-Cyclodextrin

TABLE II-continued

α-D-Glucose
α-D-Glucose-1-Phosphate
α-D-Lactose
α-Hydroxybutyric Acid
α-Keto Butyric Acid
α-Keto Glutaric Acid
α-Keto Valeric Acid
α-Ketoglutaric Acid
α-Ketovaleric Acid
α-Methyl-DGalactoside
α-Methyl-DGlucoside
α-Methyl-DMannoside
β-Cyclodextrin
β-Hydroxybutyric Acid
β-Methyl-DGalactoside
β-Methyl-D-Glucoside
γ-Amino Butyric Acid
γ-Hydroxybutyric Acid
(2-amino-3,4-dihydroxy-5-hydroxymethyl-1-cyclohexyl)glucopyranoside
(3,4-disinapoyl)fructofuranosyl-(6-sinapoyl)glucopyranoside
(3-sinapoyl)fructofuranosyl-(6-sinapoyl)glucopyranoside
1 reference
1,10-di-O-(2-acetamido-2-deoxyglucopyranosyl)-2-azi-1,10-decanediol
1,3-mannosylmannose
1,6-anhydrolactose
1,6-anhydrolactose hexaacetate
1,6-dichlorosucrose
1-chlorosucrose
1-desoxy-1-glycinomaltose
1-O-alpha-2-acetamido-2-deoxygalactopyranosyl-inositol
1-O-methyl-di-N-trifluoroacetyl-beta-chitobioside
1-propyl-4-O-beta galactopyranosyl-alpha galactopyranoside
2-(acetylamino)-4-O-(2-(acetylamino)-2-deoxy-4-O-sulfogalactopyranosyl)-2-deoxyglucose
2-(trimethylsilyl)ethyl lactoside
2,1',3',4',6'-penta-O-acetylsucrose
2,2'-O-(2,2'-diacetamido-2,3,2',3'-tetradeoxy-6,6'-di-O-(2-tetradecylhexadecanoyl)-alpha,alpha'-trehalose-3,3'-diyl)bis(N-lactoyl-alanyl-isoglutamine)
2,3,6,2',3',4',6'-hepta-O-acetylcellobiose
2,3'-anhydrosucrose
2,3-di-O-phytanyl-1-O-(mannopyranosyl-(2-sulfate)-(1-2)-glucopyranosyl)-sn-glycerol
2,3-epoxypropyl O-galactopyranosyl(1-6)galactopyranoside
2,3-isoprolylideneerthrofuranosyl 2,3-O-isopropylideneerythrofuranoside
2',4'-dinitrophenyl 2-deoxy-2-fluoro-beta-xylobioside
2,5-anhydromannitol iduronate
2,6-sialyllactose
2-acetamido-2,4-dideoxy-4-fluoro-3-O-galactopyranosylglucopyranose
2-acetamido-2-deoxy-3-O-(gluco-4-enepyranosyluronic acid)glucose
2-acetamido-2-deoxy-3-O-rhamnopyranosylglucose
2-acetamido-2-deoxy-6-O-beta galactopyranosylgalactopyranose
2-acetamido-2-deoxyglucosylgalactitol
2-acetamido-3-O-(3-acetamido-3,6-dideoxy-beta-glucopyranosyl)-2-deoxy-galactopyranose
2-amino-6-O-(2-amino-2-deoxy-glucopyranosyl)-2-deoxyglucose
2-azido-2-deoxymannopyranosyl-(1,4)-rhamnopyranose
2-deoxy-6-O-(2,3-dideoxy-4,6-O-isopropylidene-2,3-(N-tosylepimino)-mannopyranosyl)-4,5-O-isopropylidene-1,3-di-N-tosylstreptamine
2-deoxymaltose
2-iodobenzyl-1-thiocellobioside
2-N-(4-benzoyl)benzoyl-1,3-bis(mannos-4-yloxy)-2-propylamine
2-nitrophenyl-2-acetamido-2-deoxy-6-O-beta galactopyranosyl-alpha galactopyranoside
2-O-(glucopyranosyluronic acid)xylose
2-O-glucopyranosylribitol-1-phosphate
2-O-glucopyranosylribitol-4'-phosphate
2-O-rhamnopyranosyl-rhamnopyranosyl-3-hydroxyldecanoyl-3-hydroxydecanoate
2-O-talopyranosylmannopyranoside
2-thiokojibiose
2-thiosophorose
3,3'-neotrehalosadiamine
3,6,3',6'-dianhydro(galactopyranosylgalactopyranoside)
3,6-di-O-methyl-beta-glucopyranosyl-(1-4)-2,3-di-O-methyl-alpha-rhamnopyranose
3-amino-3-deoxyaltropyranosyl-3-amino-3-deoxyaltropyranoside
3-deoxy-3-fluorosucrose
3-deoxy-5-O-rhamnopyranosyl-2-octulopyranosonate
3-deoxyoctulosonic acid-(alpha-2-4)-3-deoxyoctulosonic acid TABLE II-continued 3-deoxysucrose
3-ketolactose
3-ketosucrose
3-ketotrehalose
3-methyllactose
3-O-(2-acetamido-6-O-(N-acetylneuraminyl)-2-deoxygalactosyl)serine
3-O-(glucopyranosyluronic acid)galactopyranose
3-O-beta-glucuronosylgalactose
3-O-fucopyranosyl-2-acetamido-2-deoxyglucopyranose
3'-O-galactopyranosyl-1-4-O-galactopyranosylcytarabine
3-O-galactosylarabinose
3-O-talopyranosylmannopyranoside
3-trehalosamine
4-(trifluoroacetamido)phenyl-2-acetamido-2-deoxy-4-O-beta-mannopyranosyl-beta-glucopyranoside
4,4',6,6'-tetrachloro-4,4',6,6'-tetradeoxygalactotrehalose
4,6,4',6'-dianhydro(galactopyranosylgalactopyranoside)
4,6-dideoxysucrose
4,6-O-(1-ethoxy-2-propenylidene)sucrose hexaacetate
4-chloro-4-deoxy-alpha-galactopyranosyl3,4-anhydro-1,6-dichloro-1,6-dideoxy-beta-lyxo-hexulofuranoside
4-glucopyranosylmannose
4-methylumbelliferylcellobioside
4-nitrophenyl 2-fucopyranosyl-fucopyranoside
4-nitrophenyl 2-O-alpha-D-galactopyranosyl-alpha-D-mannopyranoside
4-nitrophenyl 2-O-alpha-D-glucopyranosyl-alpha-D-mannopyranoside
4-nitrophenyl 2-O-alpha-D-mannopyranosyl-alpha-D-mannopyranoside
4-nitrophenyl 6-O-alpha-D-mannopyranosyl-alpha-D-mannopyranoside
4-nitrophenyl-2-acetamido-2-deoxy-6-O-beta-D-galactopyranosyl-beta-D-glucopyranoside
4-O-(2-acetamido-2-deoxy-beta-glucopyranosyl)ribitol
4-O-(2-amino-2-deoxy-alpha-glucopyranosyl)-3-deoxy-manno-2-octulosonic acid
4-O-(glucopyranosyluronic acid)xylose
4-O-acetyl-alpha-N-acetylneuraminyl-(2-3)-lactose
4-O-alpha-D-galactopyranosyl-D-galactose
4-O-galactopyranosyl-3,6-anhydrogalactose dimethylacetal
4-O-galactopyranosylxylose
4-O-mannopyranosyl-2-acetamido-2-deoxyglucose
4-thioxylobiose
4-trehalosamine
4-trifluoroacetamidophenyl 2-acetamido-4-O-(2-acetamido-2-deoxyglucopyranosyl)-2-deoxymannopyranosiduronic acid
5-bromoindoxyl-beta-cellobioside
5'-O-(fructofuranosyl-2-1-fructofuranosyl)pyridoxine
5-O-beta-galactofuranosyl-galactofuranose
6 beta-galactinol
6(2)-thiopanose
6,6'-di-O-corynomycoloyl-alpha-mannopyranosyl-alpha-mannopyranoside
6,6-di-O-maltosyl-beta-cyclodextrin
6,6'-di-O-mycoloyl-alpha-mannopyranosyl-alpha-mannopyranoside
6-chloro-6-deoxysucrose
6-deoxy-6-fluorosucrose
6-deoxy-alpha-gluco-pyranosiduronic acid
6-deoxy-gluco-heptopyranosyl 6-deoxy-gluco-heptopyranoside
6-deoxysucrose
6-O-decanoyl-3,4-di-O-isobutyrylsucrose
6-O-galactopyranosyl-2-acetamido-2-deoxygalactose
6-O-galactopyranosylgalactose
6-O-heptopyranosylglucopyranose
6-thiosucrose
7-O-(2-amino-2-deoxyglucopyranosyl)heptose
8-methoxycarbonyloctyl-3-O-glucopyranosyl-mannopyranoside
8-O-(4-amino-4-deoxyarabinopyranosyl)-3-deoxyoctulosonic acid
allolactose
allosucrose
allyl 6-O-(3-deoxyoct-2-ulopyranosylonic acid)-(1-6)-2-deoxy-2-(3-hydroxytetradecamido)glucopyranoside 4-phosphate
alpha-(2-9)-disialic acid
alpha,alpha-trehalose 6,6'-diphosphate
alpha-glucopyranosyl alpha-xylopyranoside
alpha-maltosyl fluoride
aprosulate
benzyl 2-acetamido-2-deoxy-3-O-(2-O-methyl-beta-galactosyl)-beta-glucopyranoside
benzyl 2-acetamido-2-deoxy-3-O-beta fucopyranosyl-alpha-galactopyranoside
benzyl 2-acetamido-6-O-(2-acetamido-2,4-dideoxy-4-fluoroglucopyranosyl)-2-deoxygalactopyranoside TABLE II-continued benzyl gentiobioside
beta-D-galactosyl(1-3)-4-nitrophenyl-N-acetyl-alpha-D-galactosamine
beta-methylmelibiose
calcium sucrose phosphate
camiglibose
cellobial
cellobionic acid
cellobionolactone
Cellobiose
cellobiose octaacetate
cellobiosyl bromide heptaacetate
Celsior
chitobiose
chondrosine
Cristolax
deuterated methyl beta-mannobioside
dextrin maltose
D-glucopyranose, O-D-glucopyranosyl
Dietary Sucrose
difructose anhydride I
difructose anhydride III
difructose anhydride IV
digalacturonic acid
DT 5461
ediol
epilactose
epsilon-N-1-(1-deoxylactulosyl)lysine
feruloyl arabinobiose
floridoside
fructofuranosyl-(2-6)-glucopyranoside
FZ 560
galactosyl-(1-3)galactose
garamine
gentiobiose
geranyl 6-O-alpha-L-arabinopyranosyl-beta-D-glucopyranoside
geranyl 6-O-xylopyranosyl-glucopyranoside
glucosaminyl-1,6-inositol-1,2-cyclic monophosphate
glucose
glucosyl (1-4) N-acetylglucosamine
glucuronosyl(1-4)-rhamnose
heptosyl-2-keto-3-deoxyoctonate
inulobiose
Isomaltose
isomaltulose
isoprimeverose
kojibiose
lactobionic acid
lacto-N-biose II
Lactose
lactosylurea
Lactulose
laminaribiose
lepidimoide
leucrose
levanbiose
lucidin 3-O-beta-primveroside
LW 10121
LW 10125
LW 10244
maltal
maltitol
Maltose
maltose hexastearate
maltose-maleimide
maltosylnitromethane heptaacetate
maltosyltriethoxycholesterol
maltotetraose
Malun 25
mannosucrose
mannosyl-(1-4)-N-acetylglucosaminyl-(1-N)-urea
mannosyl(2)-N-acetyl(2)-glucose
melibionic acid
Melibiose
melibiouronic acid
methyl 2-acetamido-2-deoxy-3-O-(alpha-idopyranosyluronic acid)-4-O-sulfo-beta-galactopyranoside
methyl 2-acetamido-2-deoxy-3-O-(beta-glucopyranosyluronic acid)-4-O-sulfo-beta-galactopyranoside
methyl 2-acetamido-2-deoxy-3-O-glucopyranosyluronoyl-glucopyranoside

TABLE II-continued methyl 2-O-alpha-rhamnopyranosyl-beta-galactopyranoside
methyl 2-O-beta-rhamnopyranosyl-beta-galactopyranoside
methyl 2-O-fucopyranosylfucopyranoside 3 sulfate
methyl 2-O-mannopyranosylmannopyranoside
methyl 2-O-mannopyranosyl-rhamnopyranoside
methyl 3-O-(2-acetamido-2-deoxy-6-thioglucopyranosyl)-galactopyranoside
methyl 3-O-galactopyranosylmannopyranoside
methyl 3-O-mannopyranosylmannopyranoside
methyl 3-O-mannopyranosyltalopyranoside
methyl 3-O-talopyranosyltalopyranoside
methyl 4-O-(6-deoxy-manno-heptopyranosyl)galactopyranoside
methyl 6-O-acetyl-3-O-benzoyl-4-O-(2,3,4,6-tetra-O-benzoyl-galactopyranosyl)-2-deoxy-2-phthalimidoglucopyranoside
methyl 6-O-mannopyranosylmannopyranoside
methyl beta-xylobioside
methyl fucopyranosyl(1-4)-2-acetamido-2-deoxyglucopyranoside
methyl laminarabioside
methyl O-(3-deoxy-3-fluorogalactopyranosyl)(1-6)galactopyranoside
methyl-2-acetamido-2-deoxyglucopyranosyl-1-4-glucopyranosiduronic acid
methyl-2-O-fucopyranosylfucopyranoside 4-sulfate
MK 458
N(1)-2-carboxy-4,6-dinitrophenyl-N(6)-lactobionoyl-1,6-hexanediamine
N-(2,4-dinitro-5-fluorophenyl)-1,2-bis(mannos-4'-yloxy)propyl-2-amine
N-(2'-mercaptoethyl)lactamine
N-(2-nitro-4-azophenyl)-1,3-bis(mannos-4'-yloxy)propyl-2-amine
N-(4-azidosalicylamide)-1,2-bis(mannos-4'-yloxy)propyl-2-amine
N,N-diacetylchitobiose
N-acetylchondrosine
N-acetyldermosine
N-acetylgalactosaminyl-(1-4)-galactose
N-acetylgalactosaminyl-(1-4)-glucose
N-acetylgalactosaminyl-1-4-N-acetylglucosamine
N-acetylgalactosaminyl-1-4-N-acetylglucosamine
N-acetylgalactosaminyl-alpha(1-3)galactose
N-acetylglucosamine-N-acetylmuramyl-alanyl-isoglutaminyl-alanyl-glycerol dipalmitoyl
N-acetylglucosaminyl beta(1-6)N-acetylgalactosamine
N-acetylglucosaminyl-1-2-mannopyranose
N-acetylhyalobiuronic acid
N-acetylneuraminoyllactose
N-acetylneuraminoyllactose sulfate ester
N-acetylneuraminyl-(2-3)-galactose
N-acetylneuraminyl-(2-6)-galactose
N-benzyl-4-O-(beta-galactopyranosyl)glucamine-N-carbodithioate
neoagarobiose
N-formylkansosaminyl-(1-3)-2-O-methylrhamnopyranose
O-((Nalpha)-acetylglucosamine 6-sulfate)-(1-3)-idonic acid
O-(4-O-feruloyl-alpha-xylopyranosyl)-(1-6)-glucopyranose
O-(alpha-idopyranosyluronic acid)-(1-3)-2,5-anhydroalditol-4-sulfate
O-(glucuronic acid 2-sulfate)-(1--3)-O-(2,5)-andydrotalitol 6-sulfate
O-(glucuronic acid 2-sulfate)-(1--4)-O-(2,5)-anhydromannitol 6-sulfate
O-alpha-glucopyranosyluronate-(1-2)-galactose
O-beta-galactopyranosyl-(1-4)-O-beta-xylopyranosyl-(1-0)-serine
octyl maltopyranoside
O-demethylpaulomycin A
O-demethylpaulomycin B
O-methyl-di-N-acetyl beta-chitobioside
Palatinit
paldimycin
paulomenol A
paulomenol B
paulomycin A
paulomycin A2
paulomycin B
paulomycin C
paulomycin D
paulomycin E
paulomycin F
phenyl 2-acetamido-2-deoxy-3-O-beta-D-galactopyranosyl-alpha-D-galactopyranoside
phenyl O-(2,3,4,6-tetra-O-acetylgalactopyranosyl)-(1-3)-4,6-di-O-acetyl-2-deoxy-2-phthalimido-1-thioglucopyranoside
poly-N-4-vinylbenzyllactonamide
pseudo-cellobiose
pseudo-maltose
rhamnopyranosyl-(1-2)-rhamnopyranoside-(1-methyl ether)
rhoifolin
ruberythric acid
S-3105
senfolomycin A
senfolomycin B
solabiose
SS 554
streptobiosamine
Sucralfate
Sucrose
sucrose acetate isobutyrate
sucrose caproate
sucrose distearate
sucrose monolaurate
sucrose monopalmitate
sucrose monostearate
sucrose myristate
sucrose octaacetate
sucrose octabenzoic acid
sucrose octaisobutyrate
sucrose octasulfate
sucrose polyester
sucrose sulfate
swertiamacroside
T-1266
tangshenoside I
tetrahydro-2-((tetrahydro-2-furanyl)oxy)-2H-pyran
thionigerose
Trehalose
trehalose 2-sulfate
trehalose 6,6'-dipalmitate
trehalose-6-phosphate
trehalulose
trehazolin
trichlorosucrose
tunicamine
turanose
U 77802
U 77803
xylobiose
xylose-glucose
xylosucrose In certain embodiments, *Botryococcus braunii* is cultured using glucose, mannose, galactose, fructose, or glycerol, or a combination thereof, as the fixed carbon source. Optionally urea can be added to the media as well. Preferably, such cultures are grown in the dark, i.e., once culturing is begun, no light is permitted to strike the microalgae.

In other embodiments, other components are added to the media including, but not limited to, dextrin, malt extract, traders yeast, corn meal, corn steep powder, whole dead yeast, casein type M, casein type B, tomato paste, molasses, soy hydrolysate, soy flour, corn starch and maltose.

An exemplary vector design for expression of a gene in microalgae contains a first gene encoding a transporter in operable linkage with a promoter active in microalgae. Alternatively, if the vector does not contain a promoter in operable linkage with the first gene, the first gene can be transformed into the cells such that it becomes operably linked to an endogenous promoter at the point of vector integration. The promoterless method of transformation has been proven to work in microalgae (see for example Plant Journal 14:4, (1998), pp. 441-447), though the frequency of transformation is lower using this method than when using a promoter active in microalgae in operable linkage with the first gene. The vector can also contain a second gene encodes a protein that imparts resistance to an antibiotic or herbicide. Optionally, either gene is followed by a 3' untranslated sequence containing a polyadenylation signal. Expression cassettes encoding the two genes can be physically linked in the vector or on separate vectors. Co-transformation of microalgae can also be used, in which distinct vector molecules are simultaneously used to transform cells (see for example Protist. 2004

December; 155(4):381-93). The transformed cells can be optionally selected based upon the ability to grow in the presence of the antibiotic or other selectable marker under conditions in which cells lacking the resistance cassette would not grow, such as in the dark. Including of the selectable marker is optional because obligate photoautotrophism provides an alternative means to select for expression of a sugar transporter. Correct expression and functionality of the transporter as well as the ability to metabolize transported fixed carbon is the selectable phenotype when cells are grown in the absence of light for photosynthesis.

DNA encoding the transporter and resistance gene is preferably codon-optimized cDNAs. Methods of recoding genes for expression in microalgae are described in US Patent Application 20040209256. Additional information is available at the web address www.kazusa.or.jp/codon.

Many promoters in expression vectors are active in microalgae, including both promoters that are endogenous to the algae being transformed algae as well as promoters that are not endogenous to the algae being transformed (i.e., promoters from other algae, promoters from higher plants, and promoters from plant viruses or algae viruses). Exogenous and/or endogenous promoters that are active in microalgae, and antibiotic resistance genes functional in microalgae are described by e.g., Curr Microbiol. 1997 December; 35(6): 356-62 (*Chlorella vulgaris*); Mar Biotechnol (NY). 2002 January; 4(1):63-73 (*Chlorella ellipsoidea*); Mol Gen Genet. 1996 Oct. 16; 252(5):572-9 (*Phaeodactylum tricornutum*); Plant Mol. Biol. 1996 April; 31(1):1-12 (*Volvox carteri*); Proc Natl Acad Sci USA. 1994 Nov. 22; 91(24):11562-6 (*Volvox carteri*); Falciatore A, Casotti R, Leblanc C, Abrescia C, Bowler C, PMID: 10383998, 1999 May; 1(3):239-251 (Laboratory of Molecular Plant Biology, Stazione Zoologica, Villa Comunale, I-80121 Naples, Italy) (*Phaeodactylum tricornutum* and *Thalassiosira weissflogii*); Plant Physiol. 2002 May; 129(1):7-12. (*Porphyridium* sp.); Proc Natl Acad Sci USA. 2003 Jan. 21; 100(2):438-42. (*Chlamydomonas reinhardtii*); Proc Natl Acad Sci USA. 1990 February; 87(3): 1228-32. (*Chlamydomonas reinhardtii*); Nucleic Acids Res. 1992 Jun. 25; 20(12):2959-65; Mar Biotechnol (NY). 2002 January; 4(1):63-73 (*Chlorella*); Biochem Mol Biol Int. 1995 August; 36(5):1025-35 (*Chlamydomonas reinhardtii*); J. Microbiol. 2005 August; 43(4):361-5 (*Dunaliella*); Yi Chuan Xue Bao. 2005 April; 32(4):424-43 (*Dunaliella*); Mar Biotechnol (NY). 1999 May; 1(3):239-251. (*Thalassiosira* and *Phaedactylum*); Koksharova, Appl Microbiol Biotechnol 2002 February; 58(2):123-37 (various species); Mol Genet Genomics. 2004 February; 271(1):50-9 (*Thermosynechococcus elongates*); J. Bacteriol. (2000), 182, 211-215; FEMS Microbiol Lett. 2003 Apr. 25; 221(2):155-9; Plant Physiol. 1994 June; 105(2):635-41; Plant Mol. Biol. 1995 December; 29(5):897-907 (*Synechococcus* PCC 7942); Mar Pollut Bull. 2002; 45(1-12):163-7 (*Anabaena* PCC 7120); Proc Natl Acad Sci USA. 1984 March; 81(5):1561-5 (*Anabaena* (various strains)); Proc Natl Acad Sci USA. 2001 Mar. 27; 98(7): 4243-8 (*Synechocystis*); Wirth, Mol Gen Genet. 1989 March; 216(1):175-7 (various species); Mol Microbiol, 2002 June; 44(6):1517-31 and Plasmid, 1993 September; 30(2):90-105 (*Fremyella diplosiphon*); Hall et al. (1993) Gene 124: 75-81 (*Chlamydomonas reinhardtii*); Gruber et al. (1991). Current Micro. 22: 15-20; Jarvis et al. (1991) Current Genet. 19: 317-322 (*Chlorella*); for additional promoters see also Table 1 from U.S. Pat. No. 6,027,900).

The promoter used to express an exogenous gene can be the promoter naturally linked to that gene or can be a heterologous gene. Some promoters are active in more than one species of microalgae. Other promoters are species-specific. Preferred promoters include promoters such as RBCS2 from *Chlamydomonas reinhardtii* and viral promoters, such as cauliflower mosaic virus (CMV) and *chlorella* virus, which have been shown to be active in multiple species of microalgae (see for example Plant Cell Rep. 2005 March; 23(10-11):727-35; J. Microbiol. 2005 August; 43(4):361-5; Mar Biotechnol (NY). 2002 January; 4(1):63-73). In other embodiments, the *Botryococcus* malate dehydrogenase promoter, such a nucleic acid comprising any part of SEQ ID NO:1, or the *Chlamydomonas reinhardtii* RBCS2 promoter (SEQ ID NO:2) can be used. Optionally, at least 10, 20, 30, 40, 50, or 60 nucleotides or more of these sequences containing a promoter are used.

Promoters, cDNAs, and 3'UTRs, as well as other elements of the vectors, can be generated through cloning techniques using fragments isolated from native sources (see for example Molecular Cloning: A Laboratory Manual, Sambrook et al. (3d edition, 2001, Cold Spring Harbor Press; and U.S. Pat. No. 4,683,202). Alternatively, elements can be generated synthetically using known methods (see for example Gene. 1995 Oct. 16; 164(1):49-53).

Examples of genes encoding carbohydrate transporters to facilitate the uptake of exogenously provided carbohydrates include SEQ ID NOs: 3, 4, 5, 6 and 7 and allelic or species variants thereof. Other variants having a nucleic acid sequence encodes a protein with at least about 60% amino acid sequence identity with a protein with a sequence represented by one of SEQ ID NOs: 3-7. Optionally, the nucleic acid sequence encodes a protein with at least about 85%, at least about 90%, at least about 95%, or at least about 98%, or higher, amino acid identity with a sequence of these SEQ ID NOs: 3-7.

Additional examples include a *Chlorella* hexose transporter (such as Genbank Q39525), a yeast hxt2 transporter (such as Genbank P23585), a human GLUT1 (such as Genbank AA A52571), a *Nicotiana tabacum* glucose transporter (such as Genbank CAA47324), and a *Vicia faba* glucose transport protein (such as Genbank CAB07812).

Alternatively or additionally to transformation, cells can be mutagenized and then selected for the ability to grow in the absence of light energy but in the presence of a fixed carbon source. Examples of mutagenesis include contact or propagation in the presence of a mutagen, such as ultraviolet light, nitrosoguanidine, and/or ethane methyl sulfonate (EMS).

As one example, a method of the disclosure comprises providing a nucleic acid encoding a carbohydrate transporter protein containing codons preferred in *Botryococcus braunii*; transforming a *Botryococcus braunii* cell with the nucleic acid; and selecting for the ability to undergo cell division in the absence of light and in the presence of a carbohydrate that is transported by the carbohydrate transporter protein. In another example, a method comprises subjecting a microalgal cell to a mutagen; placing the cell in the presence of a fixed carbon molecule; and selecting for the ability to undergo cell division in the absence of light.

Cells can be transformed by, e.g., biolistics, electroporation, glass bead transformation and silicon carbide whisker transformation, including those referenced previously in this section.

V Engineering Cells to Increase Hydrocarbon Production

Some wild-type cells already have good growth characteristics but do not produce high yields of microorganisms or do not produce the desired type of hydrocarbons. Examples include *Pyrobotrys, Phormidium, Agmenellum, Carteria, Lepocinclis, Pyrobotrys, Nitzschia, Lepocinclis, Anabaena, Euglena, Spirogyra, Chlorococcum, Tetraedron, Oscillatoria, Phagus,* and *Chlorogonium,* which have the desirable growth characteristic of growing in municipal sewage or wastewater. Such cells can be engineered to have improved hydrocarbon production characteristics. Desired characteristics include optimizing hydrocarbon yield per unit volume and/or per unit time, carbon chain length (e.g., for gasoline production), reducing the number of double or triple bonds, optionally to zero, removing or eliminating rings and cyclic structures, increasing the hydrogen:carbon ratio of a particular species of hydrocarbon or of a population of distinct hydrocarbons, and removing oxygen atoms such as in the case of an aldehyde decarbonylase. The engineering involves transforming one or more genes encoding hydrocarbon modification enzymes such as, for example, a squalene synthase gene (see GenBank Accession number AF205791), an aldehyde decarbonylase (see GenBank Accession numbers BAA11024 and CAA03710).

TABLE III

Examples of Hydrocarbon Modification Enzymes

A. amino acid sequences contained, referenced, or encoded by nucleic acid sequences contained or referenced in any of US patents:
6,610,527
6,451,576
6,429,014
6,342,380
6,265,639
6,194,185
6,114,160
6,083,731
6,043,072
5,994,114
5,891,697
5,871,988
6,265,639

B. amino acid seqeunces of GenBank accession numbers:
AAO18435
ZP_00513891
Q38710
AAK60613
AAK60610
AAK60611
NP_113747
CAB75874
AAK60612
AAF20201
BAA11024
AF205791
CAA03710

Each of the amino acid sequences contained or encoded by nucleic acid sequences contained in the U.S. patent identified in Table IIIA is hereby incorporated by reference herein. Each of the amino acid sequences identified by the GenBank accession numbers in Table IIIB is hereby incorporated by reference herein.

Such genes can be obtained from cells already known to have good hydrocarbon production such as *Botryococcus braunii*. Genes already known to have a role in hydrocarbon production, e.g., a gene encoding an enzyme that saturates double bonds, can be transformed individually into recipient cells. However, to practice the invention it is not necessary to make a priori assumptions as to which genes are required. A library of DNA containing different genes, such as cDNAs from a good hydrocarbon production organism, can be transformed into recipient cells. The cDNA is preferably in operable linkage with a promoter active in microalgae. Examples of organisms that produce useful hydrocarbons are microalgae such as *Botryococcus braunii, Dunaliella* and *Nannochloropsis*, cells from any *Pinaceae* organism and sub-classes thereof, such as *Abies, Picea, Pinus* (such as *Pinus jeffreyi*), *Stobus*, and *Tsuga*, and other hydrocarbon-producing organisms such as *Pisum sativum*. Different recipient microalgae cells transformed by a library receive different genes from the library. For example, a population of *Botryococcus* cells transformed with a cDNA library from *Pinus jeffreyi*, which produces n-heptane, a high-energy alkane ($C_7H_{16}$), can be screened for a phenotype such as increased total hydrocarbon production, increased energy content of a crude oil preparation of a given volume compared to a similarly prepared crude hydrocarbon preparation from cells not transformed with the cDNA library, and/or direct production of n-heptane. Transformants having improved hydrocarbon production are identified though screening methods known in the art, such as, for example, HPLC, gas chromatography, and mass spectrometry methods of hydrocarbon analysis (for examples of such analysis, see Biomass and Bioenergy Vol. 6. No. 4. pp. 269-274 (1994); Experientia 38; 47-49 (1982); and Phytochemistry 65 (2004) 3159-3165). These transformants are then subjected to further transformation with the original library and/or optionally interbred to generate a further round of organisms having improved hydrocarbon production. In a preferred embodiment, *Botryococcus braunii* cells that are capable of heterotrophic growth and contain a functional carbohydrate transporter are transformed with a single exogenous gene or a cDNA library from a hydrocarbon-producing organism. General procedures for evolving whole organisms to acquire a desired property are described in e.g., U.S. Pat. No. 6,716,631. Such methods entail, e.g., introducing a library of DNA fragments into a plurality of cells, whereby at least one of the fragments undergoes recombination with a segment in the genome or an episome of the cells to produce modified cells. The modified cells are then screened for modified cells that have evolved toward acquisition of the desired function. Vectors and methods for transformation are analogous to those discussed in connection with trophic conversion.

Some microalgae produce significant quantities of polysaccharides in addition to hydrocarbons. Because polysaccharide biosynthesis can use a significant proportion of the total metabolic energy available to cells, mutagenesis of hydrocarbon-producing cells followed by screening for reduced or eliminated polysaccharide production generates novel strains that are capable of producing higher yields of hydrocarbons. For example, *Botryococcus* cells are known to produce extracellular polysaccharide.

The phenol: sulfuric acid assay detects carbohydrates (see Hellebust, Handbook of Phycological Methods, Cambridge University Press, 1978; and Cuesta G., et al., J Microbiol Methods. 2003 January; 52(1):69-73). The 1,6 dimethylmethylene blue assay detects anionic polysaccharides. (see for example Braz J Med Biol Res. 1999 May; 32(5):545-50; Clin Chem. 1986 November; 32(11):2073-6).

Polysaccharides can also be analyzed through methods such as HPLC, size exclusion chromatography, and anion exchange chromatography (see for example Prosky L, Asp N, Schweizer T F, DeVries J W & Furda I (1988) Determination of insoluble, soluble and total dietary fiber in food and food products: Interlaboratory study. Journal of the Association of Official Analytical Chemists 71, 1017±1023; Int J Biol Macromol. 2003 November; 33(1-3):9-18). Polysaccharides can also be detected using gel electrophoresis (see for example Anal Biochem. 2003 Oct. 15; 321(2):174-82; Anal Biochem. 2002 Jan. 1; 300(1):53-68).

VI Culturing Microorganisms

Microorganisms are cultured both for purposes of conducting genetic manipulations and for subsequent production of hydrocarbons. The former type of culture is conducted on a small scale and initially, at least under conditions in which the starting microorganism can grow. For example, if the starting microorganism is a photoautotroph the initial culture can be conducted in the presence of light. The culture conditions can be changed as the microorganism is evolved or engineered to grow independently of light. Culture for purposes of hydrocarbon production is usually conducted on a large scale. Preferably a fixed carbon source is present. The culture can also be exposed to light some or all of the time. In certain embodiments, a photoautotroph, such as *Botryococcus braunii* can be grown on a fixed carbon source, in the absence of light.

Microalgae can be cultured in liquid media. The culture can be contained within a fermentor or bioreactor. In particular embodiments, where light is not needed or not desired for growth, the fermentor or bioreactor does not allow light to enter. Alternatively, microalgae can also be cultured in a photofermentor or photobioreactor that contains a fixed carbon source and allow light to strike the cells. In certain embodiments, exposure of microalgae cells to light, even in the presence of a fixed carbon source that the cells transport and utilize (ie: mixotrophic growth), nonetheless accelerates growth compared to culturing cells in the dark. This is not necessarily true for *Botryococcus braunii*, which, in specific embodiments, is preferably grown in the dark when a fixed carbon source is present. Culture condition parameters can be manipulated to optimize total hydrocarbon production, the combination of hydrocarbon species produced, and/or production of a hydrocarbon species. In some instances it is preferable to culture cells in the dark, such as, for example, when using extremely large (40,000 liter and higher) fermentors or bioreactors that do not allow light to strike the culture or when culturing *Botryococcus braunii* in the presence of a fixed carbon source.

Microalgal culture media typically contains components such as a fixed nitrogen source, trace elements, optionally a buffer for pH maintenance, and phosphate. Other components can include a fixed carbon source such as acetate or glucose, and salts such as sodium chloride, particularly for seawater microalgae. Examples of trace elements include zinc, boron, cobalt, copper, manganese, and molybdenum in, for example, the respective forms of $ZnCl_2$, $H_3BO_3$, $CoCl_2.6H_2O$, $CuCl_2.2H_2O$, $MnCl_2.4H_2O$ and $(NH_4)_6Mo_7O_{24}.4H_2O$.

For organisms able to grow on a fixed carbon source, the fixed carbon source can be, for example, a carbohydrate, such as, but not limited to, glucose, fructose, sucrose, galactose, xylose, mannose, or rhamnose; N-acetylglucosamine; glycerol; floridoside; and/or glucuronic acid. The one or more carbon source(s) can be supplied at a concentration of at least about 50 µM, at least about 100 µM, at least about 500 µM, at least about 5 mM, at least about 50 mM, at least about 500 mM, or at a concentration within any range having any of these values as endpoints, of one or more exogenously provided fixed carbon source(s). Expressed as a percentage of the culture medium, the one or more carbon sources can be supplied at a concentration of about 0.1%, about 0.2%, about 0.3%, about 0.4%, about 0.5%, about 0.6%, about 0.7%, about 0.8%, about 0.9%, about 1.0%, about 1.2%, about 1.5%, about 1.7%, about 2%, about 3%, about 4%, about 5%, or at a concentration within any range having any of these values as endpoints. The carbon source can be provided to the medium at these concentrations, without further addition of carbon source. Alternatively, the concentration of the carbon source(s) can be controlled during culture to be within a range having any of these values as endpoints. Some microalgae species, e.g., *Botryococcus braunii*, can grow by utilizing a fixed carbon source such as glucose in the absence of light. Such growth is known as heterotrophic growth.

Some microorganisms naturally grow on or can be engineered to grow on a fixed carbon source that is a heterogeneous source of compounds such as municipal waste, secondarily treated sewage, wastewater, and other sources of fixed carbon and other nutrients such as sulfates, phosphates, and nitrates. Microorganisms that are grown in media that comprises sewage, such as secondarily treated sewage are particularly useful. The sewage component serves as a nutrient source in the production of hydrocarbons, and the culture provides an inexpensive source of hydrocarbons.

Other culture parameters can also be manipulated, such as the pH of the culture media, the identity and concentration of trace elements and other media constituents.

Microalgae can be grown in the presence of light. The number of photons striking a culture of microalgae cells can be manipulated, as well as other parameters such as the wavelength spectrum and ratio of dark:light hours per day. Microalgae can also be cultured in natural light, as well as simultaneous and/or alternating combinations of natural light and artificial light. For example, microalgae of the genus *Chlorella* can be cultured under natural light during daylight hours and under artificial light during night hours.

The gas content of a fermentor, bioreactor, photofermentor, or photobioreactor to grow microorganisms like microalgae can be manipulated. Part of the volume of a photobioreactor can contain gas rather than liquid. Gas inlets can be used to pump gases into the photobioreactor. Any gas can be pumped into a photobioreactor, including air, air/$CO_2$ mixtures, noble gases such as argon and others. The rate of entry of gas into a fermentor, bioreactor, photofermentor, or photobioreactor can also be manipulated. Increasing gas flow into a fermentor, bioreactor, photofermentor, or photobioreactor increases the turbidity of a culture of microalgae. Placement of ports conveying gases into a fermentor, bioreactor, photofermentor, or photobioreactor can also affect the turbidity of a culture at a given gas flow rate. Air/$CO_2$ mixtures can be modulated to generate optimal amounts of $CO_2$ for maximal growth by a particular organism. Microalgae grow significantly faster in the light under, for example, 3% $CO_2$/97% air than in 100% air. 3% $CO_2$/97% air is approximately 100-fold more $CO_2$ than found in air. For example, air:$CO_2$ mixtures of about 99.75% air:0.25% $CO_2$, about 99.5% air:0.5% $CO_2$, about 99.0% air:1.00% $CO_2$, about 98.0% air:2.0% $CO_2$, about 97.0% air:3.0% $CO_2$, about 96.0% air:4.0% $CO_2$, and about 95.00% air:5.0% $CO_2$ can be infused into a fermentor, bioreactor, photofermentor, or photobioreactor.

Microalgae cultures can also be subjected to mixing using devices such as spinning blades and impellers, rocking of a culture, stir bars, infusion of pressurized gas, and other instruments. Optionally, a fermentor, bioreactor, photofermentor, or photobioreactor apparatus of the invention comprises one or more of these devices such that the device(s) may be permanently attached to the apparatus or may be separate initially but are later joined to form a complete apparatus.

The invention includes a fermentor, bioreactor, photofermentor, or photobioreactor comprising a culture medium containing a fixed carbon source and a hydrocarbon-producing microalgae as described herein. Optionally, the fixed carbon source is a carbohydrate, such as a monosaccharide or disaccharide as a non-limiting example. Non-limiting examples include glucose, mannose, galactose, fructose, xylose, arabinose, sucrose, or other carbohydrates in Table II herein. In some embodiments, the microalgae is capable of metabolizing the carbohydrate or monosaccharide as a carbon source. Non-limiting examples include recombinantly modified microalgae that are able to utilize the carbohydrate or monosaccharide as a fixed carbon source. In other embodiments, the microalgae is part of a combination of the invention comprising a first microalgae and a second microbe. The mixture of medium, carbohydrate, and microalgae (and optional second microbe) may be in a vessel, or first location, of the fermentor, bioreactor, photofermentor, or photobioreactor.

A fermentor, bioreactor, photofermentor, or photobioreactor may be part of a system of the invention. The system may comprise a number of vessels. A first vessel may be one in which a polysaccharide is hydrolyzed by an enzyme into monosaccharides. Alternatively, monosaccharides or a monosaccharide:oligosaccharide mixture such as depolymerized cellulose can be provided directly into the system. A second vessel may be one in which the monosaccharides or monosaccharide:oligosaccharide mixture are incubated with a hydrocarbon-producing microalgae capable of using the monosaccharides or monosaccharide:oligosaccharide mixture as a fixed carbon source to produce microalgal biomass. A third vessel may be one in which distinct species of hydrocarbons that have been extracted from the microalgal biomass are separated or fractionated from each other. In some embodiments, the distinct species of hydrocarbons are separated or fractionated based upon the boiling temperatures of each species, such as a distillation column, also known as a fractional distillation column. For example, oil refineries use distillation columns to fractionate crude oil into different products. Distillation columns used in oil refineries are typically large, vertical cylindrical columns with diameters ranging from about 65 centimeters to 6 meters and heights ranging from about 6 meters to 60 meters or more. The distillation columns have liquid outlets at intervals up the column which allow for the withdrawal of different fractions or products having different boiling points or boiling ranges. The "lightest" products (those with the lowest boiling point) exit from the top of the columns and the "heaviest" products (those with the highest boiling point) exit from the bottom of the column. Fractional distillation is used in oil refineries to separate crude oil into useful substances (or fractions) having different hydrocarbons of different boiling points.

Methods for the growth and propagation of *Botryococcus braunii* are known (see for example Largeau et al., Phytochemistry, 1980, 19:1043-1051 and Metzger et al. Phytochemistry, 1985, 24(10):2305-2312). The invention also provides novel growth conditions for *Botryococcus*. For example, *Botryococcus braunii* can be grown in the dark in the presence of a fixed carbon source. Alternatively or additionally, this species can be grown under conditions comprising an increased amount of cobalt, which can be an essential factor in the synthesis of long chain hydrocarbons. An increased amount of cobalt above about 5 nM, above about 10 nM, above about 100 nM, above about 1 µM, above about 10 µM, above about 100 µM, above about 1 mM, above about 10 mM, and above about 100 mM elemental cobalt can be used. Cobalt can be provided to cells in the form of, for example, $CoCl_2 \cdot 6H_2O$.

For hydrocarbon production, cells, including recombinant cells of the invention described herein, are preferably cultured or fermented in large quantities. The culturing may be in large liquid volumes, such as in suspension cultures as an example. Other examples include starting with a small culture of cells which expand into a large biomass in combination with cell growth and propagation as well as hydrocarbon production. Bioreactors or steel fermentors can be used to accommodate large culture volumes. A fermentor similar those used in the production of beer and/or wine is suitable, as are extremely large fermentors used in the commercial production of ethanol.

Appropriate nutrient sources for culture in a fermentor are provided. These include raw materials such as one or more of the following: a fixed carbon source such as glucose, corn starch, cellulose, depolymerized cellulose as described herein (comprising a mixture of glucose and xylose), sucrose, sugar cane, sugar beet, lactose, milk whey, or molasses; a fat source, such as fats or vegetable oils; a nitrogen source, such as protein, soybean meal, cornsteep liquor, hydrolyzed casein, urea, ammonia (pure or in salt form), nitrate or nitrate salt, or molecular nitrogen; and a phosphorus source, such as phosphate salts. Additionally, a fermenter allows for the control of culture conditions such as temperature, pH, oxygen tension, and carbon dioxide levels. Optionally, gaseous components, like oxygen or nitrogen, can be bubbled through a liquid culture. In certain embodiments, *Botryococcus braunii* is cultured in the dark with a fixed carbon source and a complex nitrogen source, such as hydrolyzed casein, and/or urea.

Thus the invention includes a method for producing hydrocarbons via a fermentor or bioreactor with one or more of the above features, such as growth in the absence of light, the inclusion of cobalt in the culture conditions; inoculation with a hydrocarbon-producing microalgae, such as *Botryococcus braunii* or one or more recombinant cells of the invention described herein; and use of appropriate nutrient sources, including a fixed carbon source, a nitrogen source, and a phosphorus source. Of course a method for producing hydrocarbons may comprise a combination of two or more, or all of the above, features.

In some embodiments, the method comprises a) providing culture media that comprised a carbohydrate or one or more species of monosaccharides as a fixed carbon source, in a fermenter; b) inoculating the fermenter with a hydrocarbon-producing microalgae capable of metabolizing the carbohydrate or monosaccharide(s) as a carbon source; c) culturing the microalgae for a period of time to generate microalgal biomass; d) separating or extracting or isolating hydrocarbons from the microalgal biomass; and e) refining the separated, extracted, or isolated hydrocarbons. In an alternative embodiment, the method comprises a) combining, in a fermentor, a carbohydrate or one or more species of monosaccharides in a culture medium with a hydrocarbon-producing microalgae capable of metabolizing the carbohydrate or monosaccharide(s) as a carbon source to form a mixture; b) culturing the microalgae in said mixture to produce hydrocarbon containing microalgal biomass; c) separating or isolating hydrocarbons from said biomass; and d) refining the separated or isolated hydrocarbons.

Non-limiting examples of a monosaccharide for use in a disclosed method include glucose, xylose, and arabinose. A disaccharide that can be used is sucrose. In other embodiments, the carbohydrate is selected from Table II herein. Non-limiting examples of a fermenter include a photobioreactor or a fermenter that allows culturing of the microalgae without light exposure thereto. The microalgae may thus be cultured without light that strikes them or in the absence of light.

In many embodiments, the microalgae is selected from Table I herein. In some methods, the microalgae is *Botryococcus braunii*. In other embodiments, the microalgae has been transformed with an exogenous gene encoding a carbohydrate transporter as described herein.

In further embodiments, the method may further comprise the hydrolysis of a polysaccharide to produce a carbohydrate or monosaccharide for the culture media. The hydrolysis may be by any methodology known to the skilled person, including, but not limited to, enzyme catalyzed hydrolysis. In some embodiments, the hydrolysis is mediated by one or more enzymes, such as, but not limited to, the 74 polysaccharide-degrading enzymes from *Aspergillus nidulans, Aspergillus fumigatus*, and *Neurospora crassa* as described by Bauer et al. ("Development and application of a suite of polysaccharide-degrading enzymes for analyzing plant cell walls." *Proc Natl Acad Sci USA*. 2006, 103(30):11417-22. Epub 2006 Jul. 14). Non-limiting examples of a polysaccharide for use in the method include corn starch and cellulose. In some cases, the method comprises the use of corn starch or cellulose as the polysaccharide and enzymes which degrade it to produce glucose.

The separating, extracting, or isolating of hydrocarbons from the biomass may by via any methodology known to the skilled person. Non-limiting examples include the harvesting methodologies described below. In some embodiments, the methodology comprises hexane extraction, pressing the biomass, or by in vivo extraction (see for example, European Patent Application EP20030721175 entitled "Process for continuous production and extraction of carotenoids from natural sources." and discussion of in vivo extraction from living cells in the section below). The separated, extracted, or isolated hydrocarbons may be refined by any methodology known to the skilled person. Non-limiting examples of refining include cracking the hydrocarbons, as described herein, and the separating of different hydrocarbon species by use of a fractional distillation column.

A fermentor or bioreactor can be used to allow cells to undergo the various phases of their growth cycle. As an example, an inoculum of hydrocarbon-producing cells can be introduced into a medium followed by a lag period (lag phase) before the cells begin growth. Following the lag period, the growth rate increases steadily and enters the log, or exponential, phase. The exponential phase is in turn followed by a slowing of growth due to decreases in nutrients and/or increases in toxic substances. After this slowing, growth stops, and the cells enter a stationary phase or steady state. The amount of biomass in stationary phase is generally constant unless there is cell lysis.

Hydrocarbon production by cells disclosed herein occur mainly during the log phase and sometimes thereafter, including the stationary phase wherein nutrients are supplied, or still available, to allow the continuation of hydrocarbon production in the absence of cell growth.

Mixotrophic growth is the use of both light and fixed carbon source(s) as energy sources for cells to grow and produce hydrocarbons. Mixotrophic growth can be conducted in a photofermentor or photobioreactor. Microalgae can be grown and maintained in closed photobioreactors made of different types of transparent or semitransparent material. Such material can include Plexiglas® enclosures, glass enclosures, bags made from substances such as polyethylene, transparent or semitransparent pipes, and other materials. Microalgae can be grown and maintained in open photofermentors or photobioreactors such as raceway ponds, settling ponds, and other non-enclosed containers.

Fermentors, bioreactors, photofermentors, or photobioreactors can have ports allowing entry of gases, solids, semi-solids and liquids into the chamber containing the microalgae. Ports are usually attached to tubing or other means of conveying substances. Gas ports, for example, convey gases into the culture. Pumping gases into a fermentor, bioreactor, photofermentor, or photobioreactor can serve to both feed cells $CO_2$ and other gases and to aerate the culture and therefore generate turbidity. The amount of turbidity of a culture varies as the number and position of gas ports is altered. For example, gas ports can be placed along the bottom of a cylindrical polyethylene bag. Microalgae grow faster when $CO_2$ is added to air and bubbled into a photobioreactor. For example, a 5% $CO_2$:95% air mixture is infused into a fermentor, bioreactor, photofermentor, or photobioreactor containing *Botryococcus* cells (see for example J Agric Food Chem. 2006 Jun. 28; 54(13):4593-9; J Biosci Bioeng. 1999; 87(6):811-5; and J Nat. Prod. 2003 June; 66(6):772-8).

Photobioreactors or photofermentors can be exposed to one or more light sources to provide microalgae with light as an energy source via light directed to a surface of the photobioreactor or photofermentor. Preferably the light source provides an intensity that is sufficient for the cells to grow, but not so intense as to cause oxidative damage or cause a photoinhibitive response. In some instances a light source has a wavelength range that mimics or approximately mimics the range of the sun. In other instances a different wavelength range utilized by the microalgae is used. Photobioreactors or photofermentors can be placed outdoors or in a greenhouse or other facility that allows sunlight to strike the surface. Preferred photon intensities for species of the genus *Botryococcus* are between 25 and 500 $\mu E \, m^{-2} \, s^{-1}$ (see for example Photosynth Res. 2005 June; 84(1-3):21-7).

Fermentors, bioreactors, photofermentors, or photobioreactors preferably have one or more ports that allow media entry. It is not necessary that only one substance enter or leave a port. For example, a port can be used to flow culture media into the fermentor, bioreactor, photofermentor, or photobioreactor and then later can be used for sampling, gas entry, gas exit, or other purposes. In some instances a fermentor, bioreactor, photofermentor, or photobioreactor is filled with culture media at the beginning of a culture and no more growth media is infused after the culture is inoculated. In other words, the microalgal biomass is cultured in an aqueous medium for a period of time during which the microalgae reproduce and increase in number; however quantities of aqueous culture medium are not flowed through the fermentor, bioreactor, photofermentor, or photobioreactor throughout the time period. Thus in some embodiments, aqueous culture medium is not flowed through the fermentor, bioreactor, photofermentor, or photobioreactor after inoculation.

In other instances culture media can be flowed though the fermentor, bioreactor, photofermentor, or photobioreactor throughout the time period during which the microalgae reproduce and increase in number. In some embodiments media is infused into the fermentor, bioreactor, photofermentor, or photobioreactor after inoculation but before the cells reach a desired density. In other words, a turbulent flow regime of gas entry and media entry is not maintained for reproduction of microalgae until a desired increase in number of said microalgae has been achieved.

Fermentors, bioreactors, photofermentors, or photobioreactors preferably have one or more ports that allow gas entry. Gas can serve to both provide nutrients such as $CO_2$ as well as to provide turbulence in the culture media. Turbulence can be achieved by placing a gas entry port below the level of the aqueous culture media so that gas entering the fermentor, bioreactor, photofermentor, or photobioreactor bubbles to the surface of the culture. One or more gas exit ports allow gas to escape, thereby preventing pressure buildup in the fermentor, bioreactor, photofermentor, or photobioreactor. Preferably a gas exit port leads to a "one-way" valve that prevents contaminating microorganisms to enter the fermentor, bioreactor, photofermentor, or photobioreactor. In some instances cells are cultured in a fermentor, bioreactor, photofermentor, or photobioreactor for a period of time during which the microalgae reproduce and increase in number; however a turbulent flow regime with turbulent eddies predominantly throughout the culture media caused by gas entry is not maintained for all of the period of time. In other instances a turbulent flow regime with turbulent eddies predominantly throughout the culture media caused by gas entry can be maintained for all of the period of time during which the microalgae reproduce and increase in number. In some instances a predetermined range of ratios between the scale of the fermentor, bioreactor, photofermentor, or photobioreactor and the scale of eddies is not maintained for the period of time during which the microalgae reproduce and increase in number. In other instances such a range can be maintained.

Fermentors, bioreactors, photofermentors, or photobioreactors preferably have at least one port that can be used for sampling the culture. Preferably a sampling port can be used repeatedly without compromising the axenic nature of the culture. A sampling port can be configured with a valve or other device that allows the flow of sample to be stopped and started. Alternatively a sampling port can allow continuous sampling. Fermentors, bioreactors, photofermentors, or photobioreactors preferably have at least one port that allows inoculation of a culture. Such a port can also be used for other purposes such as media or gas entry.

VII Harvesting

Hydrocarbons produced by cells of the invention can be harvested, or otherwise collected, by any convenient means. For example, hydrocarbons secreted from cells can be centrifuged to separate the hydrocarbons in a hydrophobic layer from contaminants in an aqueous layer and optionally from any solid materials as a precipitate after centrifugation. Extracellular hydrocarbons can also be separated by tangential flow filtration. Preferred organisms for culturing in fermentors, bioreactors, photofermentors, or photobioreactors to produce hydrocarbons include those disclosed herein. Material containing cell or cell fractions can be treated with proteases to degrade contaminating proteins before or after centrifugation. In some instances the contaminating proteins are associated, possibly covalently, to hydrocarbons or hydrocarbon precursors which form hydrocarbons upon removal of the protein. In other instances the hydrocarbon molecules are in a preparation that also contains proteins. Proteases can be added to hydrocarbon preparations containing proteins to degrade proteins (for example, the protease from *Streptomyces griseus* can be used (SigmaAldrich catalog number P5147). After digestion, the hydrocarbons are preferably purified from residual proteins, peptide fragments, and amino acids. This purification can be accomplished, for example, by methods listed above such as centrifugation and filtration.

Hydrocarbons can also be isolated by whole cell extraction. The cells are first disrupted and then intracellular and cell membrane/cell wall-associated hydrocarbons as well as extracellular hydrocarbons can be collected from the whole cell mass, such as by use of centrifugation as described above.

Alternatively, cells can be homogenized to facilitate hydrocarbon collection. As a non-limiting example, a pressure disrupter can be used to pump a cell-containing slurry through a restricted orifice valve. High pressure (up to 1500 bar) is applied, followed by an instant expansion through an exiting nozzle. Cell disruption is accomplished by three different mechanisms: impingement on the valve, high liquid shear in the orifice, and sudden pressure drop upon discharge, causing an explosion of the cell. The method releases intracellular molecules.

Alternatively, a ball mill can be used. In a ball mill, cells are agitated in suspension with small abrasive particles. Cells break because of shear forces, grinding between beads, and collisions with beads. The beads disrupt the cells to release cellular contents. In some embodiments, a sample is cryogenically ball milled in a planetary ball mill (Retsch, PM100) at 10-80 grams per batch size. The powder is placed in a grinding bowl with eight to ten ¾-inch-diameter stainless steel balls. The sample is cooled repeatedly with liquid nitrogen. The material was milled at 400-550 rpm for about 30 to about 60 min. The final product was dried in a desiccator overnight.

Cells can also by lysed with high frequency sound. The sound can be produced electronically and transported through a metallic tip to an appropriately concentrated cellular suspension. This sonication (or ultrasonication) disrupts cellular integrity based on the creation of cavities in cell suspension. Cells can also be disrupted by shear forces, such as with the use of blending (such as with a high speed or Waring blender as examples), the french press, or even centrifugation in case of weak cell walls, to disrupt cells.

Various methods are available for separating hydrocarbons from cellular lysates produced by the above methods. For example, hydrocarbons can be extracted with a hydrophobic solvent like hexane (see Frenz et al. 1989, Enzyme Microb. Technol., 11:717). Hydrocarbons can also be extracted using liquefaction (see for example Sawayama et al. 1999, Biomass and Bioenergy 17:33-39 and Inoue et al. 1993, Biomass Bioenergy 6(4):269-274); oil liquefaction (see for example Minowa et al. 1995, Fuel 74(12):1735-1738); and supercritical $CO_2$ extraction (see for example Mendes et al. 2003, Inorganica Chimica Acta 356:328-334).

Hexane solvent extraction can be used in isolation or it can be used along with the oil press/expeller method. After the oil has been extracted using an expeller, the remaining pulp can be mixed with hexane to extract the remaining oil content. The oil dissolves in the cyclohexane, and the pulp is filtered out from the solution. The oil and hexane are then separated by means of distillation.

Another method of oil extraction is the supercritical fluid/carbon dioxide extraction method, in which carbon dioxide is liquefied under pressure and heated to the point that it has the properties of both a liquid and gas. This liquefied fluid then acts as the solvent in extracting the oil from the algal biomass.

Solventless extraction of hydrocarbons can also be used, such as the methods described in U.S. Pat. No. 6,750,048.

Extracellular hydrocarbons can also be extracted in vivo from living microalgae cells which are then returned to a fermentor or bioreactor by exposure of the cells, in an otherwise sterile environment, to a non-toxic extraction solvent, followed by separation of the living cells and the hydrophobic fraction of extraction solvent and hydrocarbons, wherein the separated living cells are then returned to a culture container such as a stainless steel fermenter or bioreactor or photobioreactor or photofermentor (see Biotechnol Bioeng. 2004 Dec. 5; 88(5):593-600 and Biotechnol Bioeng. 2004 Mar. 5; 85(5): 475-81). Such in vivo extraction is also described in European patent application EP20030721175 20030507 entitled "PROCESS FOR CONTINUOUS PRODUCTION AND EXTRACTION OF CAROTENOIDS FROM NATURAL SOURCES".

Hydrocarbons can also be extracted from algal biomass by pressing of material. When algae is dried it retains its oil content, which then can be pressed out with an oil press. For example, commercial manufacturers of vegetable oil use a combination of mechanical pressing and chemical solvents in extracting oil. For representative oil presses, see IBG Monforts Oekotec GmbH & Co., Germany. Also see for example U.S. Pat. Nos. 5,186,722; 5,939,571; and 5,077,071.

VIII Modification of Hydrocarbons Produced by Cells

Hydrocarbons produced by cells as described herein can be modified by the use of one or more enzymes. When the hydrocarbons are in the extracellular environment of the cells, one or more enzymes can be added to that environment under conditions in which the enzyme modifies the hydrocarbon or completes its synthesis from a hydrocarbon precursor. Alternatively, the hydrocarbons can be partially, or completely, isolated from the cellular material before addition of one or more enzymes. Such enzymes are exogenously added, and their enzymatic activity occurs outside the cell or in vitro.

Suitable examples of enzymes for use in modifying hydrocarbons include those which saturate carbon-carbon double, or triple, bonds in hydrocarbon molecules; and enzymes listed in Table III as well as allelic and species variants thereof. In further embodiments, the enzyme is squalene synthase, as GenBank accession number AAF20201, and species and allelic variants thereof, or other variants exhibiting at least 70% with AAF202201 and have squalene synthase activity. Alternatively, the enzyme can be a terpene synthase, such as, but not limited to, a polypeptide that has at least 70% amino acid identity with the sequence found as GenBank accession numbers AAO18435, ZP_00513891, and Q38710, or allelic or species variants of any of these, and exhibits terpene synthase activity. Alternatively, the enzyme can be an aldehyde decarbonylase such as GenBank Accession numbers BAA11024 and CAA03710), or a polypeptide that has at least 70% amino acid identity with one of GenBank Accession numbers BAA11024 or CAA03710 that exhibits aldehyde decarbonylase activity. In additional embodiments, the enzymatic activity is present in a sequence that has at least about 70%, at least about 80%, at least about 85%, at least about 90%, at least about 95%, or at least about 99% identity with one of the above described sequences, all of which are hereby incorporated by reference as if fully set forth.

A substrate and/or cofactor of an enzyme can also be added for use in combination with the enzyme. Examples of a substrate or cofactor include NADPH, NADH, ATP, or cobalt or cobalt ion. Optionally, the substrate and/or cofactor can be produced in situ by an added cell free extract. Optionally, the substrate and/or cofactor is produced by an added product of co-cultured cells.

IX Additional Processing/Extraction

Hydrocarbons produced by cells in vivo, or enzymatically modified in vitro, as described herein can be optionally further processed by conventional means. The processing can include "cracking" to reduce the size, and thus increase the hydrogen:carbon ratio, of hydrocarbon molecules. Catalytic and thermal cracking methods are routinely used in hydrocarbon processing. Catalytic methods involve the use of a catalyst, such as a solid acid catalyst. The catalyst can be silica-alumina or a zeolite, which result in the heterolytic, or asymmetric, breakage of a carbon-carbon bond to result in a carbocation and a hydride anion. These reactive intermediates then undergo either rearrangement or hydride transfer with another hydrocarbon. The reactions can thus regenerate the intermediates to result in a self-propagating chain mechanism. Hydrocarbons can also be processed to reduce, optionally to zero, the number of carbon-carbon double, or triple, bonds therein. Hydrocarbons can also be processed to remove or eliminate a ring or cyclic structure therein. Hydrocarbons can also be processed to increase the hydrogen:carbon ratio. This can include the addition of hydrogen ("hydrogenation") and/or the "cracking" of hydrocarbons into smaller hydrocarbons.

Thermal methods involve the use of elevated temperature and pressure to reduce hydrocarbon size. An elevated temperature of about 800° C. and pressure of about 700 kPa can be used. These conditions generate "light," a term that is sometimes used to refer to hydrogen-rich hydrocarbon molecules (as distinguished from photon flux), while also generating, by condensation, heavier hydrocarbon molecules which are relatively depleted of hydrogen. The methodology provides homolytic, or symmetrical, breakage and produces alkenes, which may be optionally enzymatically saturated as described above.

Catalytic and thermal methods are standard in plants for hydrocarbon processing and oil refining. Thus hydrocarbons produced by cells as described herein can be collected and processed or refined via conventional means. See Hillen et al. (Biotechnology and Bioengineering, Vol. XXIV:193-205 (1982)) for a report on hydrocracking of $B.$ $braunii$ produced hydrocarbons. In alternative embodiments, the fraction is treated with another catalyst, such as an organic compound, heat, and/or an inorganic compound.

X Hydrocarbon Compositions

In certain embodiments, practice of the above methods results in hydrocarbon compositions different in type and/or quantity than those produced by conventional methods. As discussed above, such compositions can be provided purified in whole or in part from one or more components normally found with the hydrocarbons. Examples include compositions of materials from cell culture, which may include cells, cell fragments, intracellular components, and culture media components. Optionally components of hydrocarbon compositions include botryococcene, squalene, and/or farnesyl diphosphate. Final products can include any of the fractions conventionally distilled from crude oil as discussed above. As an example, co-expression of a glucose transporter and an aldehyde decarbonylase in $B.$ $braunii$ in the presence of exogenously provided glucose generates significantly more hydrocarbon molecules containing only carbon and hydrogen per unit volume of culture per unit time than can be produced by culturing wild-type $B.$ $braunii$. The resulting, novel hydrocarbon compositions are an aspect of the invention. Expression of an aldehyde decarbonylase by a promoter that is active constitutively allows for continuous catalytic transformation of numerous species of aldehydes to alkanes at all phases of the cell cycle. Aldehyde decarbonylases catalyze the decarbonylation of aldehydes to form alkanes or alkenes and carbon monoxide. This reaction increases the overall energy content of a hydrocarbon preparation containing aldehydes.

In vitro processing of hydrocarbons produced by microorganisms via enzymes or other means is usually incomplete, giving rise to a mixed population of hydrocarbons. Some of the hydrocarbons produced in such a population remain in the form produced in vivo by a microorganism. Other hydrocarbons in the population initially produced in vivo have undergone further processing in vitro and differ from the hydrocarbons resulting solely from in vivo processing.

All references cited herein, including patents, patent applications, and publications, are hereby incorporated by reference in their entireties, whether previously specifically incorporated or not. The publications mentioned herein are cited for the purpose of describing and disclosing reagents, methodologies and concepts that may be used in connection with the present invention. Nothing herein is to be construed as an admission that these references are prior art in relation to the inventions described herein.

Although this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

Example 1

The methods here can be used to GE the bug with other valuable genes such as: and name a few. Boiler plate out of the other application.

A *Botryococcus braunii* codon-optimized synthetic cDNA encoding the protein of SEQ ID NO:3 is placed in operable linkage with a first promoter of SEQ ID NO:2. A cDNA identical to GenBank accession number AF205791 (encoding squalene synthase) is cloned into the same plasmid in operable linkage with a second promoter of SEQ ID NO:2.

The resulting nucleic acid vector is used to transform *Botryococcus braunii* cells (strain UTEX-2441) via biolistic transformation as described in Zaslayskai a et al. Science (2001) 292:2073-2075. Cells are plated on 4×mCHU agar media (see Phytochemistry, 1980, Vol. 19, pp. 1043-1051) containing 0.5% glucose. Plates are stored in the dark. Colonies of trophically converted *B. braunii* are recovered from plates and streak purified on new plates to isolate single colonies.

A transgenic strain exhibiting heterotrophic growth is cultured in an Erlenmeyer flask in the dark in 4×mCHU media containing 0.5% glucose. Also grown in parallel is a culture of wild type *Botryococcus braunii* (UTEX 2441) in the presence of 125 µE/s/m$^2$ light. After the cultures reach plateau density they are harvested. Cell pellets are extracted with hexane by the method of Biomass and Bioenergy, Vol. 6. No. 4., pp. 269-274 (1994). Oil preparations are then analyzed by gas chromatography as described in Phytochemistry 65 (2004) 3159-3165. The preparations from the transgenic strain are a composition comprising hydrocarbon molecules extracted from a plurality of transgenic microalgae cells, wherein each cell contains a first exogenous gene encoding a carbohydrate transporter that enables the cell to grow heterotrophically in the presence of a carbohydrate that is transported by the transporter and a second exogenous gene encoding a hydrocarbon modification enzyme; and the composition contains a novel hydrocarbon molecule not found in non-transgenic microalgae cells of the same species; and/or a greater amount of an endogenous hydrocarbon molecule per cell relative to other hydrocarbons found in non-transgenic microalgae cells of the same species.

Example 2

Heterotrophic Growth of *Botryococcus braunii*

Background:

*Botryococcus braunii*, a unicellular green alga, has been known to be an obligate autotroph. It was believed to require light energy to fix $CO_2$ to grow or that genetic engineering of the microalgae with a sugar (e.g., hexose or pentose) transporter would be necessary to grow *B. braunii* in the dark. However, we found *B. braunii* can grow heterotrophically with fixed carbon sources in the dark without the need for genetic engineering. This is an important finding since it provides a new way to culture *B. braunii* and an opportunity to obtain high density cultures of *B. braunii* using fermentation equipment.

Strains

Three *Botryococcus braunii* strains (UTEX 572, UTEX 2441, and N-836). UTEX 572 and UTEX 2441 are available from The University of Texas at Austin, The Culture Collection of Algae (UTEX), 1 University Station A6700, Austin, Tex. 78712-0183 USA. N-836 is available from MICROBIAL CULTURE COLLECTION, National Institute for Environmental Studies, 16-2 Onogawa, Tsukuba, Ibaraki, 305-8506 JAPAN.

Media

Modified BG-11 (17.65 mM NaNO$_3$, 0.23 mM K2PO4, 0.3 mM MgSO$_4$.7H$_2$O, 0.25 mM CaCl$_2$.2H$_2$O, 0.189 mM Na$_2$CO$_3$, 0.03 mM citric acid monohydrate, 0.023 mM ferric ammonium citrate, 0.046 mM H$_3$BO$_3$, 9.15 µM MnCl$_2$.4H$_2$O, 0.77 µM ZnSO$_4$.7H$_2$O, 0.32 CuSO$_4$.5H$_2$O, 0.21 µM CoCl$_2$.6H$_2$O, 1.62 µM NaMoO$_4$.2H$_2$O, 2.69 µM Na$_2$EDTA, 9 mg/l Tricine, 1.99 µM Thiamine-HCl, 0.006 µM Cyanocobalamine, 0.044 µM Calcium Pantothenate, 0.29 µM p-aminobenzoic acid, soil water). This was prepared by adding soil water and vitamin mix to basic BG11 for better growth support (recipe available from American Type Culture Collection (ATCC), P.O. Box 1549, Manassas, Va. 20108 USA.

Mixotrophic Condition

In the past, growth with fixed carbon sources in the light has been explored. We have tested mannose, fructose, galactose, glycerol, acetate and glucose in BG11 media and cultured UTEX 2441 in light. In the mixotrophic condition, fixed carbons other than glycerol showed inhibitory effects on growth. The experiment was repeated with UTEX 572 and UTEX 2441 for glycerol. Whereas UTEX 572 showed a marginal difference in growth with or without glycerol, UTEX 2441 showed 66% increased growth with glycerol. Dry cell weight (DCW) were measured after three weeks for the glycerol samples.

TABLE 4

Mixotrophic growth of *B. braunii* with glycerol
A. UTEX 572
B. UTEX 2441

| | DCW mg/15 ml. | DCW g/L |
|---|---|---|
| A. | | |
| 0.75% glycerol | 4.1 | 0.273 |
| 0.75% glycerol | 3.1 | 0.206 |
| 1% glycerol | 4.0 | 0.267 |
| 1% glycerol | 3.0 | 0.20 |
| 1.5% glycerol | 3.6 | 0.24 |
| 1.5% glycerol | 4.4 | 0.293 |
| BG11 only | 3.1 | 0.206 |
| BG11 only | 2.7 | 0.18 |
| BG11 only | 3.3 | 0.22 |
| B. | | |
| 0.75% glycerol | 4.1 | 0.273 |
| 0.75% glycerol | 4.3 | 0.286 |
| 1% glycerol | 3.3 | 0.22 |
| 1% glycerol | 4.8 | 0.32 |
| 1.5% glycerol | 4.3 | 0.24 |
| 1.5% glycerol | 4.7 | 0.286 |
| BG11 only | 1.7 | 0.113 |
| BG11 only | 1.4 | 0.093 |
| BG11 only | 1.4 | 0.093 |

Heterotrophic Growth of *B. braunii*

We tested heterotrophic growth of *B. braunii* with glucose. This experiment was done in a 24 well plate with 1 ml of BG11 plus glucose in the dark or light. Different concentrations of glucose (0.1, 0.5, 1%) were tested. Both strains clearly grew in the dark, showing best growth with 1% glucose. However, no growth in either strains with glucose in the light was observed. Dry cell weight (DCW) was used to measure cell growth after 4 weeks of growth (Table 5).

TABLE 5

DCW measurement of UTEX 572 (A) and UTEX 2441 (B) culture grown in the dark

|  | DCW mg/ml. | DCW g/L |
|---|---|---|
| A. | | |
| 0.1% glucose | 0.2 | 0.2 |
| 0.2% glucose | 0.2 | 0.2 |
| 0.5% glucose | 0.4 | 0.4 |
| 1.0% glucose |  | ND[†] |
| no glucose | −0.2 | −0.2 |
| B. | | |
| 0.1% glucose | 0.3 | 0.3 |
| 0.2% glucose | 0.3 | 0.3 |
| 0.5% glucose | 0.1 | 0.1 |
| 1.0% glucose | 0.7 | 0.7 |
| no glucose | 0 | 0 |

[†]culture used to inoculate 20 mL culture

Improvement of Heterotrophic Growth by Culture Passage 1 ml of UTEX 572 culture grown in 1% glucose in the dark from the previous experiment was passaged three times in the dark with 1% glucose which yielded a higher density culture with better growth rate. The heterotrophic culture was also expanded from 1 ml to 400 ml.

Optimization of Heterotrophic Growth of *B. braunii*

We tested complex nitrogen sources (urea and hydrolysate casein) on heterotrophic growth of *B. braunii* with glucose. The following experiment was done with UTEX 572, UTEX 2441, and N-836 in 20 ml of BG11 plus:

1% glucose
1% glucose+2 g/L hydrolyzed casein
1% glucose+10 mM urea

After 4 weeks, UTEX 572 showed 76% increased growth with 10 mM urea over glucose only culture, and UTEX 2441 and N-836 showed increased growth with 2 g/L hydrolysate casein to 340% and 61% respectively. Control cultures of all three strains (BG11 only) showed no growth in the dark. The results are summarized below in Table 6.

TABLE 6

Effects of urea and hydrolysate casein on heterotrophic growth of *B. braunii* measured by DCW. A. UTEX 572, B. UTEX 2441, and C. N-836.

|  | DCW mg/3 ml. | DCW g/L |
|---|---|---|
| A. UTEX 572 | | |
| 1% glucose | 0.6 | 0.20 |
| 1% glucose | 1.0 | 0.33 |
| 1% glucose + 2 g/L hydrolyzed casein | 0.5 | 0.167 |
| 1% glucose + 10 mM Urea | 1.4 | 0.467 |
| BG11 control | 0.2 | 0.066 |
| B. UTEX 2441 | | |
| 1% glucose | 0.2 | 0.067 |
| 1% glucose + 2 g/L hydrolyzed casein | 0.9 | 0.30 |
| 1% glucose + 2 g/L hydrolyzed casein | 0.9 | 0.30 |
| 1% glucose + 10 mM Urea | 0.3 | 0.10 |
| 1% glucose + 10 mM Urea | 0.2 | 0.067 |
| BG11 control | 0.2 | 0.067 |
| C. N-836 | | |
| 1% glucose | 0.8 | 0.267 |
| 1% glucose | 0.8 | 0.267 |
| 1% glucose + 2 g/L hydrolyzed casein | 1.0 | 0.33 |
| 1% glucose + 2 g/L hydrolyzed casein | 1.6 | 0.53 |
| 1% glucose + 10 mM Urea | 0.2 | 0.067 |
| 1% glucose + 10 mM Urea | 0.9 | 0.30 |
| BG11 control | 0.3 | 0.10 |

Test of Different Carbon Sources on Heterotrophic Growth of *B. braunii*.

We tested whether *B. braunii* can utilize different fixed carbon sources (mannose, glucose galactose, sodium acetate, fructose, glycerol and arabinose) for heterotrophic growth. All carbon sources were tested at three different concentrations; 0.1%, 0.5% and 1%. Cultures were grown in 24 well plates for 4 weeks in the dark in 1 ml BG11 plus fixed carbon. Control cultures were grown in BG-11 media under phototrophic conditions without a fixed carbon source. Growth was scored with +'s by visual examination of the cultures (see Table 7). UTEX 572 grew best in glucose, however there was also growth on mannose, galactose and fructose. UTEX 2441 preferred mannose in the dark but there was some growth in galactose, fructose and glycerol. N-836 demonstrated heterotrophic growth with mannose, glucose, galactose and fructose.

TABLE 7

Effect of urea carbon source on heterotrophic growth of *B. braunii*.

|  | 0.1% | 0.5% | 1% | 0.1% | 0.5% | 1% |  |
|---|---|---|---|---|---|---|---|
| A. UTEX 572 | | | | | | | |
| mannose | ++ | ++ | +++ | ++ | ++ | ++ | fructose |
| glucose | +++ | ++++ | +++++ | + | + | + | glycerol |
| galactose | ++ | +++ | +++ | + | + | + | arabinose |
| acetate | + | + | + | control | control | | |
|  |  |  |  |  |  | + |  |
| B. UTEX 2441 | | | | | | | |
| mannose | +++ | ++++ | +++++ | ++ | +++ | +++ | fructose |
| glucose | ++ | ++ | ++++ | ++ | +++ | +++ | glycerol |
| galactose | ++ | +++ | ++ | ++ | ++ | ++ | arabinose |
| acetate | ++ | ++ | ++ | control | control | | |
|  |  |  |  |  | ++ | ++ |  |
| C. N-836 | | | | | | | |
| mannose | ++ | ++ | ++ | + | + | ++ | fructose |
| glucose | ++ | ++ | +++ | + | + | + | glycerol |
| galactose | ++ | ++ | ++ | + | + | + | arabinose |
| acetate | + | + | + | control | control | | |
|  |  |  |  |  | + | + |  |

Example 3

Media Optimization for Heterotrophic Growth of *Botryococcus braunii* Media Component Screening Media components incorporated in soil bacteria media were tested in heterotrophic culture of *Botryococcus braunii* (strain UTEX 572). For each component tested, 5 ml of B11 media (as described in Example 2 above) supplemented with 3% glucose (Fisher) were prepared in 6-well plates. Additionally, the media was supplemented with 0.2% of one of the following soil bacteria media components: dextrin (MP Biomedicals), malt extract (MP Biomedicals), traders yeast (Pharmamedia), corn meal, corn steep powder (Marcor), whole dead yeast (Engevita), casein type M (Marcor), casein type B (Marcor), tomato paste, molasses, soy hydrolysate (MP Biomedicals), soy flour (Arrowhead Mills), corn starch (Sigma), and maltose (Fisher). Wells were inoculated and cultures were grown at room temperature in the dark for 16 days. Visual observation of the plates revealed better growth with maltose, soy flour, malt extract, corn starch, corn meal and dextrin conditions as compared to glucose only control. All media were filter sterilized.

The cells from each condition were transferred into 150 mL T150 flasks containing 50 mL B11 media with 3% glucose and 0.2% of their respective supplemental component. Cultures were grown in the dark for one week at 28° C. Cells were pelleted and fresh media (100 mL) were added to the cultures. The cultures were allowed to grow for another two weeks in the dark at 28° C. and then were collected and dry cell weights were measured. For most conditions, the addition of a 0.2% supplemental component increased cell growth as compared to glucose control. The components that produced the greatest increase in growth were soy flour (2 fold increase), malt extract (2 fold increase), cornstarch (2.5 fold increase) and cornmeal (3 fold increase).

High Surface to Volume Heterotrophic Cultivation of *Botryococcus braunii*.

In order to develop a reproducible, scalable process for the heterotrophic cultivation of *B. braunii*, a low-volume, slow-mixing heterotrophic procedure was developed. *Botryococcus braunii* (UTEX 572) cultures were transferred from solid media plates into 6-well plates using B-11 media supplemented with 3% glucose and was grown for one week at room temperature in the dark. The cultures were then transferred into 50 mL of fresh media in a 150 mL T-flask and agitated at 40 rpm on a plate shaker for one week at room temperature in the dark. The cultures were then transferred into 100 mL of fresh media in a 500 mL T-flask and agitated at 30 rpm with a two-inch throw for one week at room temperature in the dark. Finally, the cultures were transferred into 350 mL of fresh media in a Fernbach flask and agitated at 30 rpm with a two-inch throw for one week at room temperature in the dark. In one set of cultures, the cells were transferred into 500 mL of fresh media in a Fernbach flask (instead of 350 mL). Dry cell weights were collected for all cultures and compared. Cultures that were grown in a final volume of 350 mL of media reached a DCW of about 9 grams per liter. Interestingly, the culture with a final volume of 500 mL of media had reduced growth and only reached a DCW of about 3 grams per liter. The results suggest that the slow increase in volume of media is important to heterotrophic growth of *B. braunii*.

Sequences

```
SEQ ID NO 1: Botryococcus braunii malate dehydrogenase 5' UTR
aattggaaaccccgcgcaagaccgggttgtttggccgcctgaccggaaaggggggcctgtcccgaaggggggtctatctcttgggg gatgtcgggcgcggaaagtcgatgttgatggacctcttcttcgaccatgtcggggtcgaggccaagagccgcgtccatttcgccgagt tcatgatggaggtgaatgaccgcatcgccaccgaacgcgccaagaagcgggcgaccgatcgcccccgtcgctgcagcccttgccg aggaagtccggctgctggcgttcgacgagatgatggtgacgaacagcccggacgcgatgatcctgtcgcggctgttcaccgcgctg atcgaggcggggggtgacgatcgtcaccacctccaaccggccgcccagggatctctataagaacgggctcaaccgcgagcatttcct gcccttcatcgcgctgatcgaggcgcggctggacgtgctggcgctgaacggcccgaccgactatcggcgcgaccggctggggcg gctggacacgtggttggtgcccaatggccccaaggcgacgattaccttgtcggcggcgttcttccgcctgaccgactatccggtcgag gatgccgcgcatgtgccctctgaggacctgaaggtgggcgggcgcgtgctgaatgtccccaaggcgctgaagggcgtcgcggtctt ctcgttcaagcggttgtgcggcgaagcgcgggggggcggcggactatctggcggtcgcgcgggcttccacaccgtcatcctggtcg gaatccccaagctgggggcggagaaccgcaacgaggcggggcgcttcgtccagctgatcgacgcgctctacgaacataaggtcaa gctgctcgccgcagccgatgccagcccgccgaactctatgaaaccggcgacggccggttcgagtttgagcgcagatcagccggttg gaagagatgcgctccgaggattatctggcccaaggccatggctcggaggggccttgatcaggccttaatgcacttcgcaaccattatc gtttaaaatcttaaactctgtggaataacggttccccgacgccgcaatacacgtacgtccactacggagtaggattgga SEQ ID NO 2: RBCS2 (Rubisco) Chlamydomonas reinhardtii
cgcttagaagatttcgataaggcgccagaaggagcgcagccaaaccaggatgatgtttgatggggtatttgagcacttgcaacccttat ccggaagcccctggcccacaaaggctaggcgccaatgcaagcagttcgcatgcagccctggagcggtgccctcctgataaacc ggccaggggcctatgttctttactttttttacaagagaagtcactcaacatcttaaacggtcttaagaagtctatccgg SEQ ID NO 3: chlorella hexose transporter from Q39525 Parachlorella kessleri
maggaivasggasrsseyqggltayvllvalvaacggmllgydngvtggvasmeqferkffpdvyekkqqivetspyctydnp klqlfvsslflagliscifsawitrnwgrkasmgiggiffiaagglvnafaqdiamlivgryllgfgvglgsqvvpqylsevapfshrg mlnigyqlfvtigiliagIvnygvrnwdngwrIsIglaavpglilllgaivIpespnflvekgrtdqgrrileklrgtshveaefadiva aveiarpitmrqswrslftrrympqlltsfyiqffqqftginaiifyvpvlfsslgsassaallntvvvgavnvgstmiavllsdkfgrrf llieggitcclamlaagitlgvefgqygtedlphpvsagvlavicifiagfawswgpmgwlipseiftletrpagtavavmgnflfsf vigqafvsmlcamkfgvflffagwlvimvlcaifllpetkgvpiervqalyarhwfwkkvmgpaaqeiiaedekrvaasqaim keerisqtmk
```

-continued

SEQ ID NO 4: glucose transporter [*Arabidopsis thaliana*] GlcGalFrc from CAA390
mpaggfvvgdgqkaypgkltpfvlftcvvaamgglifgydigisggvtsmpsflkrffpsvyrkqqedastnqycqydsptltm ftsslylaalisslvastvtrkfgrrlsmlfggilfcagalingfakhvwmlivgrillgfgigfanqavplylsemapykyrgalnigfq lsitigilvaevinyffakikggwgwrlslggavvpaliitigslvlpdtpnsmiergqheeaktklrrirgvddvsqefddlvaaske sqsiehpwrnllrrkyrphltmaymipffqqltginvimfyapvlfntigfttdaslmsavvtgsvnvgativsiygvdrwgrrflfl eggtqmlicqavvaacigakfgvdgtpgelpkwyaivvvtficiyvagfawswgplgwlvpseifpleirsaaqsitvsvnmiftf iiaqifltmlchlkfglflvfaffvvvmsifvyiflpetkgipieemgqvwrshwywsrfvedgeygnalemgknsnqagtkhv SEQ ID NO 5: glucose transport protein *Vicia faba* from CAB07812
mpaagipigagnkeypgnitpfvtitcvvaamgglifgydigisggvtsmnpflekffpavyrkknaqhsknqycqydsetltlft sslylaallssvvastitrrfgrklsmlfggllflvgalinglaqnvamlivgrillgfgigfanqsvplylsemapykyrgalnigfqlsi tigilvanilnyffakikggwgwrlslggamvpaliitigslilpdtpnsmiergdrdgakaqlkrirgvedvdeefndlvaasetsm qvenpwrnllqrkyrpqltmavlipffqqftginvimfyapvlfnsigfkddaslmsavitgvvnvvatcvsiygvdkwgrralfl eggvqmlicqvavaysiaakfgtsgepgdlpkwyaivvvlficiyvagfawswgplgwlvpseifpleirsaaqsvnvsvnmlf tflvaqifltmlchmkfglflffaffvvvmtiyiytmlpetkgipieemdrvwkshpywsrfvehddngvemakggvknv SEQ ID NO 6: Galactose-H+ symporter from Q39524 *Parachlorella kessleri*
magggpvastttnrasqygyargglnwyifivaltagsgglllfgydigvtggvtsmpeflqkffpsiydrtqqpsdskdpyctydd qklqlftssfflagmfvsffagsvvrrwgrkptmliasvlflagaglnagaqdlamlvigrvllgfgvgggnnavplylsecappky rgglnmmfqlavtigiivaqlvnygtqtnanngwrlslglagvpaiillligslllpetpnslierghrrrgravlarlrrteavdtefedic aaaeestrytlrqswaalfsrqyspmlivtsliamlqqltginaimfyvpvlfssfgtarhaallntviigavnvaatfvsifsvdkfgrr glfleggiqmfigqvvtaavlgvelnkygtnlpsstaagvlvvicvyvaafawswgplgwlvpseiqtletrgagmsmavivnfl fsfvigqaflsmmcamrwgvflffagwvvimtffvyfclpetkgvpvetvptmfarhwlwgrvmgekgralvaadearkagt vafkvesgsedgkpasdq SEQ ID NO 7: ATSTP2 carbohydrate transporter *Arabidopsis thaliana* from NP_172214
mavgsmnveegtkafpakltgqvflccviaavgglmfgydigisggvtsmdtflldffphvyekkhrvhennyckfddqllqlft sslylagifasfissyvsrafgrkptimlasifflvgailnlsagelgmliggrillgfgigfgnqtvplfiseiaparyrgglnvmfqlliti gilaasyvnyltstlkngwryslggaavpalilligsffihetpasliergkdekgkqvlrkirgiedielefneikyatevatkvkspfk elftksenrpplvcgtllqffqqftginvvmfyapvlfqtmgsgdnaslistvvtngvnaiatvislllvvdfagrrcllmegalqmtat qmtiggillahlklvgpitghavr SEQ ID NO 8: yeast hexokinase from P04806
mvhlgpkkpqarkgsmadvpkelmdeihqledmftvdsetlrkvvkhfidelnkgltkkggnipmipgwvmefptgkesgn ylaidlggtnlrvvlvklsgnhtfdttqskyklphdmrttkhqeelwsfiadslkdfmveqellntkdtlplgftfsypasqnkinegi lqrwtkgfdipnveghdvvpllqneiskrelpieivalindtvgtliasyytdpetkmgvifgtgvngafydvvsdieklegkladdi psnspmainceygsfdnehlvlprtkydvavdeqsprpgqqafekmtsgyylgellrlvllelneklmlkdqdlsklkqpyim dtsyparieddpfenledtddifqkdfgvkttlperklirrlceligtraarlavcgiaaicqkrgyktghiaadgsvynkypgfkeaaa kglrdiygwtgdaskdpitivpaedgsgagaaviaalsekriaegkslgiiga

---

What is claimed is:

1. A culture of *Botryococcus braunii* microalgae produced according to the method comprising:
   providing a culture media medium that includes a fixed carbon source in a fermentor;
   inoculating the fermentor with a strain of *Botryococcus braunii* microalgae capable of metabolizing the fixed carbon source;
   culturing the microalgae in heterotrophic conditions for a period of time sufficient to produce growth and/or propagation of the microalgae, wherein the fermentor does not allow light to strike the microalgae, and
   wherein the dry cell weight of the microalgae increases by at least 2-fold as a result of the culturing.

2. The culture of claim 1, wherein the fixed carbon source comprises a carbohydrate.

3. The culture of claim 1, wherein the fixed carbon source is selected from the group consisting of glucose, mannose, galactose, fructose, glycerol, and a combination thereof.

4. The culture of claim 1, wherein the culture medium is additionally provided with a complex nitrogen source before or during culturing.

5. The culture of claim 4, wherein the complex nitrogen source is selected from the group consisting of urea, hydrolysate casein, and a combination thereof.

6. The culture of claim 1, wherein the inoculating is performed using an inoculum of *Botryococcus braunii* microalgae that has been cultured in the dark for at least one passage prior to the inoculation.

7. The culture of claim 6, wherein the inoculum has been cultured in the dark for a plurality of passages prior to addition to the fermentor.

8. The culture of claim 1, additionally comprising, after the culturing, transferring all or a portion of the microalgae to a further fermentor, and further culturing the microalgae for a period of time, wherein the further fermentor does not allow light strike the microalgae.

9. The culture of claim 1, wherein after the culturing, the dry cell weight of the microalgae is greater than the dry cell weight of the same strain of microalgae cultured in the presence of light, with all other culture conditions being the same.

10. The culture of claim 9, wherein the dry cell weight of the microalgae is at least about 2-fold greater than the dry cell weight of the same strain of microalgae cultured in the presence of light, with all other culture conditions being the same.

11. The culture of claim 1, wherein the culture medium further comprises at least one additional component selected from the group consisting of dextrin, malt extract, traders yeast, corn meal, corn steep powder, whole dead yeast, casein type M, casein type B, tomato paste, molasses, soy hydrolysate, non-fat dry milk, soy flour, corn starch and maltose.

* * * * *

SEQUENCE LISTING

<160> NUMBER OF SEQ ID NOS: 8

<210> SEQ ID NO 1
<211> LENGTH: 1113
<212> TYPE: DNA
<213> ORGANISM: Botryococcus braunii

<400> SEQUENCE: 1
aattggaaac cccgcgcaag accgggttgt ttggccgcct gaccggaaag ggggggcctg      60

```
tcccgaaggg ggtctatctc ttgggggatg tcgggcgcgg aaagtcgatg ttgatggacc      120
tcttcttcga ccatgtcggg gtcgaggcca agagccgcgt ccatttcgcc gagttcatga      180
tggaggtgaa tgaccgcatc gccaccgaac gcgccaagaa gcgggcgacc gatcgccccc      240
gtcgctgcag cccttgccga ggaagtccgg ctgctggcgt cgacgagat  gatggtgacg      300
aacagcccgg acgcgatgat cctgtcgcgg ctgttcaccg cgctgatcga ggcggggtg       360
acgatcgtca ccacctccaa ccggccgccc agggatctct ataagaacgg gctcaaccgc      420
gagcatttcc tgcccttcat cgcgctgatc gaggcgcggc tggacgtgct ggcgctgaac      480
ggcccgaccg actatcggcg cgaccggctg ggcggctgg  acacgtggtt ggtgcccaat      540
ggccccaagg cgacgattac cttgtcggcg gcgttcttcc gcctgaccga ctatccggtc      600
gaggatgccg cgcatgtgcc ctctgaggac ctgaaggtgg cgggcgcgt  gctgaatgtc      660
cccaaggcgc tgaagggcgt cgcggtcttc tcgttcaagc ggttgtgcgg cgaagcgcgg      720
ggggcggcg  actatctggc ggtcgcgcgg ggcttccaca ccgtcatcct ggtcggaatc      780
cccaagctgg gggcggagaa ccgcaacgag gcggggcgct tcgtccagct gatcgacgcg      840
ctctacgaac ataaggtcaa gctgctcgcc gcagccgatg ccagcccgcc gaactctatg      900
aaaccggcga cggccggttc gagtttgagc gcagatcagc cggttggaag agatgcgctc      960
cgaggattat ctggcccaag gccatggctc ggaggggcct tgatcaggcc ttaatgcact     1020
tcgcaaccat tatcgtttaa aatcttaaac tctgtggaat aacggttccc cgacgccgca     1080
atacacgtac gtccactacg gagtaggatt gga                                  1113

<210> SEQ ID NO 2
<211> LENGTH: 253
<212> TYPE: DNA
<213> ORGANISM: Chlamydomonas reinhardtii

<400> SEQUENCE: 2
cgcttagaag atttcgataa ggcgccagaa ggagcgcagc caaaccagga tgatgtttga       60
tggggtattt gagcacttgc aacccttatc cggaagcccc ctggcccaca aggctaggc      120
gccaatgcaa gcagttcgca tgcagcccct ggagcggtgc cctcctgata aaccggccag     180
ggggcctatg ttctttactt ttttacaaga gaagtcactc aacatcttaa acggtcttaa     240
gaagtctatc cgg                                                        253

<210> SEQ ID NO 3
<211> LENGTH: 534
<212> TYPE: PRT
<213> ORGANISM: Parachlorella kessleri

<400> SEQUENCE: 3
```

Met Ala Gly Gly Ala Ile Val Ala Ser Gly Gly Ala Ser Arg Ser Ser
1               5                   10                  15

Glu Tyr Gln Gly Gly Leu Thr Ala Tyr Val Leu Leu Val Ala Leu Val
            20                  25                  30

Ala Ala Cys Gly Gly Met Leu Leu Gly Tyr Asp Asn Gly Val Thr Gly
        35                  40                  45

Gly Val Ala Ser Met Glu Gln Phe Glu Arg Lys Phe Phe Pro Asp Val
    50                  55                  60

Tyr Glu Lys Lys Gln Gln Ile Val Glu Thr Ser Pro Tyr Cys Thr Tyr
65                  70                  75                  80

Asp Asn Pro Lys Leu Gln Leu Phe Val Ser Ser Leu Phe Leu Ala Gly

```
                       85                  90                  95
Leu Ile Ser Cys Ile Phe Ser Ala Trp Ile Thr Arg Asn Trp Gly Arg
                100                 105                 110

Lys Ala Ser Met Gly Ile Gly Gly Ile Phe Phe Ile Ala Ala Gly Gly
            115                 120                 125

Leu Val Asn Ala Phe Ala Gln Asp Ile Ala Met Leu Ile Val Gly Arg
        130                 135                 140

Val Leu Leu Gly Phe Gly Val Gly Leu Gly Ser Gln Val Val Pro Gln
145                 150                 155                 160

Tyr Leu Ser Glu Val Ala Pro Phe Ser His Arg Gly Met Leu Asn Ile
                165                 170                 175

Gly Tyr Gln Leu Phe Val Thr Ile Gly Ile Leu Ile Ala Gly Leu Val
            180                 185                 190

Asn Tyr Gly Val Arg Asn Trp Asp Asn Gly Trp Arg Leu Ser Leu Gly
        195                 200                 205

Leu Ala Ala Val Pro Gly Leu Ile Leu Leu Gly Ala Ile Val Leu
210                 215                 220

Pro Glu Ser Pro Asn Phe Leu Val Glu Lys Gly Arg Thr Asp Gln Gly
225                 230                 235                 240

Arg Arg Ile Leu Glu Lys Leu Arg Gly Thr Ser His Val Glu Ala Glu
                245                 250                 255

Phe Ala Asp Ile Val Ala Ala Val Glu Ile Ala Arg Pro Ile Thr Met
            260                 265                 270

Arg Gln Ser Trp Arg Ser Leu Phe Thr Arg Arg Tyr Met Pro Gln Leu
        275                 280                 285

Leu Thr Ser Phe Val Ile Gln Phe Gln Gln Phe Thr Gly Ile Asn
290                 295                 300

Ala Ile Ile Phe Tyr Val Pro Val Leu Phe Ser Ser Leu Gly Ser Ala
305                 310                 315                 320

Ser Ser Ala Ala Leu Leu Asn Thr Val Val Gly Ala Val Asn Val
                325                 330                 335

Gly Ser Thr Met Ile Ala Val Leu Leu Ser Asp Lys Phe Gly Arg Arg
            340                 345                 350

Phe Leu Leu Ile Glu Gly Gly Ile Thr Cys Cys Leu Ala Met Leu Ala
        355                 360                 365

Ala Gly Ile Thr Leu Gly Val Glu Phe Gly Gln Tyr Gly Thr Glu Asp
    370                 375                 380

Leu Pro His Pro Val Ser Ala Gly Val Leu Ala Val Ile Cys Ile Phe
385                 390                 395                 400

Ile Ala Gly Phe Ala Trp Ser Trp Gly Pro Met Gly Trp Leu Ile Pro
                405                 410                 415

Ser Glu Ile Phe Thr Leu Glu Thr Arg Pro Ala Gly Thr Ala Val Ala
            420                 425                 430

Val Met Gly Asn Phe Leu Phe Ser Phe Val Ile Gly Gln Ala Phe Val
        435                 440                 445

Ser Met Leu Cys Ala Met Lys Phe Gly Val Phe Leu Phe Phe Ala Gly
    450                 455                 460

Trp Leu Val Ile Met Val Leu Cys Ala Ile Phe Leu Leu Pro Glu Thr
465                 470                 475                 480

Lys Gly Val Pro Ile Glu Arg Val Gln Ala Leu Tyr Ala Arg His Trp
                485                 490                 495

Phe Trp Lys Lys Val Met Gly Pro Ala Ala Gln Glu Ile Ile Ala Glu
            500                 505                 510
```

```
Asp Glu Lys Arg Val Ala Ala Ser Gln Ala Ile Met Lys Glu Glu Arg
            515                 520                 525

Ile Ser Gln Thr Met Lys
        530

<210> SEQ ID NO 4
<211> LENGTH: 522
<212> TYPE: PRT
<213> ORGANISM: Arabidopsis thaliana

<400> SEQUENCE: 4

Met Pro Ala Gly Gly Phe Val Val Gly Asp Gly Gln Lys Ala Tyr Pro
1               5                   10                  15

Gly Lys Leu Thr Pro Phe Val Leu Phe Thr Cys Val Val Ala Ala Met
            20                  25                  30

Gly Gly Leu Ile Phe Gly Tyr Asp Ile Gly Ile Ser Gly Gly Val Thr
        35                  40                  45

Ser Met Pro Ser Phe Leu Lys Arg Phe Phe Pro Ser Val Tyr Arg Lys
    50                  55                  60

Gln Gln Glu Asp Ala Ser Thr Asn Gln Tyr Cys Gln Tyr Asp Ser Pro
65                  70                  75                  80

Thr Leu Thr Met Phe Thr Ser Ser Leu Tyr Leu Ala Ala Leu Ile Ser
                85                  90                  95

Ser Leu Val Ala Ser Thr Val Thr Arg Lys Phe Gly Arg Arg Leu Ser
            100                 105                 110

Met Leu Phe Gly Gly Ile Leu Phe Cys Ala Gly Ala Leu Ile Asn Gly
        115                 120                 125

Phe Ala Lys His Val Trp Met Leu Ile Val Gly Arg Ile Leu Leu Gly
    130                 135                 140

Phe Gly Ile Gly Phe Ala Asn Gln Ala Val Pro Leu Tyr Leu Ser Glu
145                 150                 155                 160

Met Ala Pro Tyr Lys Tyr Arg Gly Ala Leu Asn Ile Gly Phe Gln Leu
                165                 170                 175

Ser Ile Thr Ile Gly Ile Leu Val Ala Glu Val Leu Asn Tyr Phe Phe
            180                 185                 190

Ala Lys Ile Lys Gly Gly Trp Gly Trp Arg Leu Ser Leu Gly Gly Ala
        195                 200                 205

Val Val Pro Ala Leu Ile Ile Thr Ile Gly Ser Leu Val Leu Pro Asp
    210                 215                 220

Thr Pro Asn Ser Met Ile Glu Arg Gly Gln His Glu Glu Ala Lys Thr
225                 230                 235                 240

Lys Leu Arg Arg Ile Arg Gly Val Asp Asp Val Ser Gln Glu Phe Asp
                245                 250                 255

Asp Leu Val Ala Ala Ser Lys Glu Ser Gln Ser Ile Glu His Pro Trp
            260                 265                 270

Arg Asn Leu Leu Arg Arg Lys Tyr Arg Pro His Leu Thr Met Ala Val
        275                 280                 285

Met Ile Pro Phe Phe Gln Gln Leu Thr Gly Ile Asn Val Ile Met Phe
    290                 295                 300

Tyr Ala Pro Val Leu Phe Asn Thr Ile Gly Phe Thr Thr Asp Ala Ser
305                 310                 315                 320

Leu Met Ser Ala Val Val Thr Gly Ser Val Asn Val Gly Ala Thr Leu
                325                 330                 335

Val Ser Ile Tyr Gly Val Asp Arg Trp Gly Arg Arg Phe Leu Phe Leu
```

```
                        340                 345                 350
Glu Gly Gly Thr Gln Met Leu Ile Cys Gln Ala Val Val Ala Ala Cys
                355                 360                 365
Ile Gly Ala Lys Phe Gly Val Asp Gly Thr Pro Gly Glu Leu Pro Lys
            370                 375                 380
Trp Tyr Ala Ile Val Val Thr Phe Ile Cys Ile Tyr Val Ala Gly
385                 390                 395                 400
Phe Ala Trp Ser Trp Gly Pro Leu Gly Trp Leu Val Pro Ser Glu Ile
                405                 410                 415
Phe Pro Leu Glu Ile Arg Ser Ala Ala Gln Ser Ile Thr Val Ser Val
            420                 425                 430
Asn Met Ile Phe Thr Phe Ile Ile Ala Gln Ile Phe Leu Thr Met Leu
                435                 440                 445
Cys His Leu Lys Phe Gly Leu Phe Leu Val Phe Ala Phe Phe Val Val
            450                 455                 460
Val Met Ser Ile Phe Val Tyr Ile Phe Leu Pro Glu Thr Lys Gly Ile
465                 470                 475                 480
Pro Ile Glu Glu Met Gly Gln Val Trp Arg Ser His Trp Tyr Trp Ser
                485                 490                 495
Arg Phe Val Glu Asp Gly Glu Tyr Gly Asn Ala Leu Glu Met Gly Lys
            500                 505                 510
Asn Ser Asn Gln Ala Gly Thr Lys His Val
            515                 520

<210> SEQ ID NO 5
<211> LENGTH: 516
<212> TYPE: PRT
<213> ORGANISM: Vicia faba

<400> SEQUENCE: 5

Met Pro Ala Ala Gly Ile Pro Ile Gly Ala Gly Asn Lys Glu Tyr Pro
1               5                   10                  15
Gly Asn Leu Thr Pro Phe Val Thr Ile Thr Cys Val Val Ala Ala Met
                20                  25                  30
Gly Gly Leu Ile Phe Gly Tyr Asp Ile Gly Ile Ser Gly Gly Val Thr
            35                  40                  45
Ser Met Asn Pro Phe Leu Glu Lys Phe Phe Pro Ala Val Tyr Arg Lys
    50                  55                  60
Lys Asn Ala Gln His Ser Lys Asn Gln Tyr Cys Gln Tyr Asp Ser Glu
65                  70                  75                  80
Thr Leu Thr Leu Phe Thr Ser Ser Leu Tyr Leu Ala Ala Leu Leu Ser
                85                  90                  95
Ser Val Val Ala Ser Thr Ile Thr Arg Arg Phe Gly Arg Lys Leu Ser
            100                 105                 110
Met Leu Phe Gly Gly Leu Leu Phe Leu Val Gly Ala Leu Ile Asn Gly
        115                 120                 125
Leu Ala Gln Asn Val Ala Met Leu Ile Val Gly Arg Ile Leu Leu Gly
    130                 135                 140
Phe Gly Ile Gly Phe Ala Asn Gln Ser Val Pro Leu Tyr Leu Ser Glu
145                 150                 155                 160
Met Ala Pro Tyr Lys Tyr Arg Gly Ala Leu Asn Ile Gly Phe Gln Leu
                165                 170                 175
Ser Ile Thr Ile Gly Ile Leu Val Ala Asn Ile Leu Asn Tyr Phe Phe
            180                 185                 190
```

```
Ala Lys Ile Lys Gly Gly Trp Gly Trp Arg Leu Ser Leu Gly Gly Ala
        195                 200                 205

Met Val Pro Ala Leu Ile Ile Thr Ile Gly Ser Leu Ile Leu Pro Asp
    210                 215                 220

Thr Pro Asn Ser Met Ile Glu Arg Gly Asp Arg Asp Gly Ala Lys Ala
225                 230                 235                 240

Gln Leu Lys Arg Ile Arg Gly Val Glu Asp Val Glu Glu Phe Asn
                245                 250                 255

Asp Leu Val Ala Ala Ser Glu Thr Ser Met Gln Val Glu Asn Pro Trp
                260                 265                 270

Arg Asn Leu Leu Gln Arg Lys Tyr Arg Pro Gln Leu Thr Met Ala Val
                275                 280                 285

Leu Ile Pro Phe Phe Gln Gln Phe Thr Gly Ile Asn Val Ile Met Phe
    290                 295                 300

Tyr Ala Pro Val Leu Phe Asn Ser Ile Gly Phe Lys Asp Asp Ala Ser
305                 310                 315                 320

Leu Met Ser Ala Val Ile Thr Gly Val Val Asn Val Val Ala Thr Cys
                325                 330                 335

Val Ser Ile Tyr Gly Val Asp Lys Trp Gly Arg Arg Ala Leu Phe Leu
                340                 345                 350

Glu Gly Gly Val Gln Met Leu Ile Cys Gln Val Ala Val Ala Val Ser
            355                 360                 365

Ile Ala Ala Lys Phe Gly Thr Ser Gly Glu Pro Gly Asp Leu Pro Lys
    370                 375                 380

Trp Tyr Ala Ile Val Val Leu Phe Ile Cys Ile Tyr Val Ala Gly
385                 390                 395                 400

Phe Ala Trp Ser Trp Gly Pro Leu Gly Trp Leu Val Pro Ser Glu Ile
                405                 410                 415

Phe Pro Leu Glu Ile Arg Ser Ala Ala Gln Ser Val Asn Val Ser Val
                420                 425                 430

Asn Met Leu Phe Thr Phe Leu Val Ala Gln Ile Phe Leu Thr Met Leu
                435                 440                 445

Cys His Met Lys Phe Gly Leu Phe Leu Phe Ala Phe Phe Val Val
    450                 455                 460

Val Met Thr Ile Tyr Ile Tyr Thr Met Leu Pro Glu Thr Lys Gly Ile
465                 470                 475                 480

Pro Ile Glu Glu Met Asp Arg Val Trp Lys Ser His Pro Tyr Trp Ser
                485                 490                 495

Arg Phe Val Glu His Asp Asp Asn Gly Val Glu Met Ala Lys Gly Gly
                500                 505                 510

Val Lys Asn Val
        515

<210> SEQ ID NO 6
<211> LENGTH: 540
<212> TYPE: PRT
<213> ORGANISM: Parachlorella kessleri

<400> SEQUENCE: 6

Met Ala Gly Gly Gly Pro Val Ser Thr Thr Thr Asn Arg Ala Ser
1               5                   10                  15

Gln Tyr Gly Tyr Ala Arg Gly Gly Leu Asn Trp Tyr Ile Phe Ile Val
                20                  25                  30

Ala Leu Thr Ala Gly Ser Gly Gly Leu Leu Phe Gly Tyr Asp Ile Gly
            35                  40                  45
```

-continued

Val Thr Gly Gly Val Thr Ser Met Pro Glu Phe Leu Gln Lys Phe Phe
 50                  55                  60

Pro Ser Ile Tyr Asp Arg Thr Gln Gln Pro Ser Asp Ser Lys Asp Pro
65                  70                  75                  80

Tyr Cys Thr Tyr Asp Asp Gln Lys Leu Gln Leu Phe Thr Ser Ser Phe
                85                  90                  95

Phe Leu Ala Gly Met Phe Val Ser Phe Phe Ala Gly Ser Val Val Arg
            100                 105                 110

Arg Trp Gly Arg Lys Pro Thr Met Leu Ile Ala Ser Val Leu Phe Leu
        115                 120                 125

Ala Gly Ala Gly Leu Asn Ala Gly Ala Gln Asp Leu Ala Met Leu Val
130                 135                 140

Ile Gly Arg Val Leu Leu Gly Phe Val Gly Gly Gly Asn Asn Ala
145                 150                 155                 160

Val Pro Leu Tyr Leu Ser Glu Cys Ala Pro Pro Lys Tyr Arg Gly Gly
                165                 170                 175

Leu Asn Met Met Phe Gln Leu Ala Val Thr Ile Gly Ile Ile Val Ala
            180                 185                 190

Gln Leu Val Asn Tyr Gly Thr Gln Thr Met Asn Asn Gly Trp Arg Leu
        195                 200                 205

Ser Leu Gly Leu Ala Gly Val Pro Ala Ile Ile Leu Leu Ile Gly Ser
210                 215                 220

Leu Leu Leu Pro Glu Thr Pro Asn Ser Leu Ile Glu Arg Gly His Arg
225                 230                 235                 240

Arg Arg Gly Arg Ala Val Leu Ala Arg Leu Arg Arg Thr Glu Ala Val
                245                 250                 255

Asp Thr Glu Phe Glu Asp Ile Cys Ala Ala Ala Glu Glu Ser Thr Arg
            260                 265                 270

Tyr Thr Leu Arg Gln Ser Trp Ala Ala Leu Phe Ser Arg Gln Tyr Ser
        275                 280                 285

Pro Met Leu Ile Val Thr Ser Leu Ile Ala Met Leu Gln Gln Leu Thr
290                 295                 300

Gly Ile Asn Ala Ile Met Phe Tyr Val Pro Val Leu Phe Ser Ser Phe
305                 310                 315                 320

Gly Thr Ala Arg His Ala Ala Leu Leu Asn Thr Val Ile Ile Gly Ala
                325                 330                 335

Val Asn Val Ala Ala Thr Phe Val Ser Ile Phe Ser Val Asp Lys Phe
            340                 345                 350

Gly Arg Arg Gly Leu Phe Leu Glu Gly Gly Ile Gln Met Phe Ile Gly
        355                 360                 365

Gln Val Val Thr Ala Ala Val Leu Gly Val Glu Leu Asn Lys Tyr Gly
370                 375                 380

Thr Asn Leu Pro Ser Ser Thr Ala Ala Gly Val Leu Val Ile Cys
385                 390                 395                 400

Val Tyr Val Ala Ala Phe Ala Trp Ser Trp Gly Pro Leu Gly Trp Leu
                405                 410                 415

Val Pro Ser Glu Ile Gln Thr Leu Glu Thr Arg Gly Ala Gly Met Ser
            420                 425                 430

Met Ala Val Ile Val Asn Phe Leu Phe Ser Phe Val Ile Gly Gln Ala
        435                 440                 445

Phe Leu Ser Met Met Cys Ala Met Arg Trp Gly Val Phe Leu Phe Phe
450                 455                 460

```
Ala Gly Trp Val Val Ile Met Thr Phe Phe Val Tyr Phe Cys Leu Pro
465                 470                 475                 480

Glu Thr Lys Gly Val Pro Val Glu Thr Val Pro Thr Met Phe Ala Arg
            485                 490                 495

His Trp Leu Trp Gly Arg Val Met Gly Glu Lys Gly Arg Ala Leu Val
            500                 505                 510

Ala Ala Asp Glu Ala Arg Lys Ala Gly Thr Val Ala Phe Lys Val Glu
            515                 520                 525

Ser Gly Ser Glu Asp Gly Lys Pro Ala Ser Asp Gln
530                 535                 540

<210> SEQ ID NO 7
<211> LENGTH: 383
<212> TYPE: PRT
<213> ORGANISM: Arabidopsis thaliana

<400> SEQUENCE: 7

Met Ala Val Gly Ser Met Asn Val Glu Glu Gly Thr Lys Ala Phe Pro
1               5                   10                  15

Ala Lys Leu Thr Gly Gln Val Phe Leu Cys Cys Val Ile Ala Ala Val
            20                  25                  30

Gly Gly Leu Met Phe Gly Tyr Asp Ile Gly Ile Ser Gly Gly Val Thr
        35                  40                  45

Ser Met Asp Thr Phe Leu Leu Asp Phe Phe Pro His Val Tyr Glu Lys
50                  55                  60

Lys His Arg Val His Glu Asn Asn Tyr Cys Lys Phe Asp Asp Gln Leu
65                  70                  75                  80

Leu Gln Leu Phe Thr Ser Ser Leu Tyr Leu Ala Gly Ile Phe Ala Ser
                85                  90                  95

Phe Ile Ser Ser Tyr Val Ser Arg Ala Phe Gly Arg Lys Pro Thr Ile
            100                 105                 110

Met Leu Ala Ser Ile Phe Phe Leu Val Gly Ala Ile Leu Asn Leu Ser
            115                 120                 125

Ala Gln Glu Leu Gly Met Leu Ile Gly Gly Arg Ile Leu Leu Gly Phe
130                 135                 140

Gly Ile Gly Phe Gly Asn Gln Thr Val Pro Leu Phe Ile Ser Glu Ile
145                 150                 155                 160

Ala Pro Ala Arg Tyr Arg Gly Gly Leu Asn Val Met Phe Gln Phe Leu
                165                 170                 175

Ile Thr Ile Gly Ile Leu Ala Ala Ser Tyr Val Asn Tyr Leu Thr Ser
            180                 185                 190

Thr Leu Lys Asn Gly Trp Arg Tyr Ser Leu Gly Gly Ala Ala Val Pro
        195                 200                 205

Ala Leu Ile Leu Ile Gly Ser Phe Phe Ile His Glu Thr Pro Ala
210                 215                 220

Ser Leu Ile Glu Arg Gly Lys Asp Glu Lys Gly Lys Gln Val Leu Arg
225                 230                 235                 240

Lys Ile Arg Gly Ile Glu Asp Ile Glu Leu Glu Phe Asn Glu Ile Lys
                245                 250                 255

Tyr Ala Thr Glu Val Ala Thr Lys Val Lys Ser Pro Phe Lys Glu Leu
            260                 265                 270

Phe Thr Lys Ser Glu Asn Arg Pro Pro Leu Val Cys Gly Thr Leu Leu
        275                 280                 285

Gln Phe Phe Gln Gln Phe Thr Gly Ile Asn Val Val Met Phe Tyr Ala
290                 295                 300
```

```
Pro Val Leu Phe Gln Thr Met Gly Ser Gly Asp Asn Ala Ser Leu Ile
305                 310                 315                 320

Ser Thr Val Val Thr Asn Gly Val Asn Ala Ile Ala Thr Val Ile Ser
                325                 330                 335

Leu Leu Val Val Asp Phe Ala Gly Arg Arg Cys Leu Leu Met Glu Gly
                340                 345                 350

Ala Leu Gln Met Thr Ala Thr Gln Met Thr Ile Gly Gly Ile Leu Leu
            355                 360                 365

Ala His Leu Lys Leu Val Gly Pro Ile Thr Gly His Ala Val Arg
        370                 375                 380
```

<210> SEQ ID NO 8
<211> LENGTH: 485
<212> TYPE: PRT
<213> ORGANISM: Saccharomyces cerevisiae

<400> SEQUENCE: 8

```
Met Val His Leu Gly Pro Lys Lys Pro Gln Ala Arg Lys Gly Ser Met
1               5                   10                  15

Ala Asp Val Pro Lys Glu Leu Met Asp Glu Ile His Gln Leu Glu Asp
            20                  25                  30

Met Phe Thr Val Asp Ser Glu Thr Leu Arg Lys Val Val Lys His Phe
        35                  40                  45

Ile Asp Glu Leu Asn Lys Gly Leu Thr Lys Lys Gly Gly Asn Ile Pro
50                  55                  60

Met Ile Pro Gly Trp Val Met Glu Phe Pro Thr Gly Lys Glu Ser Gly
65                  70                  75                  80

Asn Tyr Leu Ala Ile Asp Leu Gly Gly Thr Asn Leu Arg Val Val Leu
                85                  90                  95

Val Lys Leu Ser Gly Asn His Thr Phe Asp Thr Thr Gln Ser Lys Tyr
            100                 105                 110

Lys Leu Pro His Asp Met Arg Thr Thr Lys His Gln Glu Glu Leu Trp
        115                 120                 125

Ser Phe Ile Ala Asp Ser Leu Lys Asp Phe Met Val Glu Gln Glu Leu
130                 135                 140

Leu Asn Thr Lys Asp Thr Leu Pro Leu Gly Phe Thr Phe Ser Tyr Pro
145                 150                 155                 160

Ala Ser Gln Asn Lys Ile Asn Glu Gly Ile Leu Gln Arg Trp Thr Lys
                165                 170                 175

Gly Phe Asp Ile Pro Asn Val Glu Gly His Asp Val Val Pro Leu Leu
            180                 185                 190

Gln Asn Glu Ile Ser Lys Arg Glu Leu Pro Ile Glu Ile Val Ala Leu
        195                 200                 205

Ile Asn Asp Thr Val Gly Thr Leu Ile Ala Ser Tyr Tyr Thr Asp Pro
210                 215                 220

Glu Thr Lys Met Gly Val Ile Phe Gly Thr Gly Val Asn Gly Ala Phe
225                 230                 235                 240

Tyr Asp Val Val Ser Asp Ile Glu Lys Leu Glu Gly Lys Leu Ala Asp
                245                 250                 255

Asp Ile Pro Ser Asn Ser Pro Met Ala Ile Asn Cys Glu Tyr Gly Ser
            260                 265                 270

Phe Asp Asn Glu His Leu Val Leu Pro Arg Thr Lys Tyr Asp Val Ala
        275                 280                 285

Val Asp Glu Gln Ser Pro Arg Pro Gly Gln Gln Ala Phe Glu Lys Met
```

```
                        290                 295                 300
Thr Ser Gly Tyr Tyr Leu Gly Glu Leu Leu Arg Leu Val Leu Leu Glu
305                 310                 315                 320

Leu Asn Glu Lys Gly Leu Met Leu Lys Asp Gln Asp Leu Ser Lys Leu
                325                 330                 335

Lys Gln Pro Tyr Ile Met Asp Thr Ser Tyr Pro Ala Arg Ile Glu Asp
                340                 345                 350

Asp Pro Phe Glu Asn Leu Glu Asp Thr Asp Asp Ile Phe Gln Lys Asp
            355                 360                 365

Phe Gly Val Lys Thr Thr Leu Pro Glu Arg Lys Leu Ile Arg Arg Leu
        370                 375                 380

Cys Glu Leu Ile Gly Thr Arg Ala Ala Arg Leu Ala Val Cys Gly Ile
385                 390                 395                 400

Ala Ala Ile Cys Gln Lys Arg Gly Tyr Lys Thr Gly His Ile Ala Ala
                405                 410                 415

Asp Gly Ser Val Tyr Asn Lys Tyr Pro Gly Phe Lys Glu Ala Ala Ala
                420                 425                 430

Lys Gly Leu Arg Asp Ile Tyr Gly Trp Thr Gly Asp Ala Ser Lys Asp
            435                 440                 445

Pro Ile Thr Ile Val Pro Ala Glu Asp Gly Ser Gly Ala Gly Ala Ala
        450                 455                 460

Val Ile Ala Ala Leu Ser Glu Lys Arg Ile Ala Glu Gly Lys Ser Leu
465                 470                 475                 480

Gly Ile Ile Gly Ala
                485
```